(12) United States Patent
Daniels et al.

(10) Patent No.: US 9,844,398 B2
(45) Date of Patent: Dec. 19, 2017

(54) SURGICAL CONNECTORS AND INSTRUMENTATION

(71) Applicant: Orthopediatrics Corp., Warsaw, IN (US)

(72) Inventors: David W. Daniels, Winona Lake, IN (US); John Kapitan, Waxhaw, NC (US); Ryan A. Lewis, Waxhaw, NC (US); John E. Pendleton, Atlanta, GA (US); John J. Souza, Waxhaw, NC (US)

(73) Assignee: OrthoPediatrics Corporation, Warsaw, IN (US)

( * ) Notice: Subject to any disclaimer, the term of this patent is extended or adjusted under 35 U.S.C. 154(b) by 69 days.

(21) Appl. No.: 14/399,060

(22) PCT Filed: May 13, 2013

(86) PCT No.: PCT/US2013/040778
§ 371 (c)(1),
(2) Date: Nov. 5, 2014

(87) PCT Pub. No.: WO2013/170262
PCT Pub. Date: Nov. 14, 2013

(65) Prior Publication Data
US 2015/0119941 A1 Apr. 30, 2015

Related U.S. Application Data

(60) Provisional application No. 61/646,030, filed on May 11, 2012, provisional application No. 61/798,414, filed on Mar. 15, 2013.

(51) Int. Cl.
A61B 17/70 (2006.01)

(52) U.S. Cl.
CPC ........ *A61B 17/7052* (2013.01); *A61B 17/708* (2013.01); *A61B 17/7056* (2013.01); *A61B 17/7082* (2013.01); *A61B 17/7086* (2013.01); *A61B 17/7037* (2013.01)

(58) Field of Classification Search
CPC .................................. A61B 17/7074–17/708
See application file for complete search history.

(56) References Cited

U.S. PATENT DOCUMENTS

| | | |
|---|---|---|
| 5,217,461 A | 6/1993 | Asher et al. |
| 5,330,473 A | 7/1994 | Howland |
| 5,498,262 A | 3/1996 | Bryan |
| 5,575,792 A | 11/1996 | Errico et al. |

(Continued)

OTHER PUBLICATIONS

Commonly-owned, co-pending PCT Patent Application Serial No. PCT/US2015/035629, filed Jun. 12, 2015.

*Primary Examiner* — Ellen C Hammond
*Assistant Examiner* — Tessa Matthews
(74) *Attorney, Agent, or Firm* — Ulmer & Berne LLP

(57) ABSTRACT

Embodiments of the present invention are directed toward a system of apparatuses to correct spinal deformities along with associated surgical techniques. The apparatuses comprise passages or channels in which spinal rods of differing diameters may be secured to allow a surgeon to vary the diameter of rods used along the length of the spine. Additionally, embodiments of the present invention are directed toward instrumentation for reduction of spinal rods into spinal pedicle screws.

14 Claims, 26 Drawing Sheets

(56) References Cited

U.S. PATENT DOCUMENTS

| | | | |
|---|---|---|---|
| 5,578,033 A | 11/1996 | Errico et al. |
| 5,601,554 A | 2/1997 | Howland et al. |
| 5,609,593 A | 3/1997 | Errico et al. |
| 5,609,594 A | 3/1997 | Errico et al. |
| 5,688,273 A | 11/1997 | Errico et al. |
| 5,688,274 A | 11/1997 | Errico et al. |
| 5,697,929 A | 12/1997 | Mellinger |
| 5,702,395 A | 12/1997 | Hopf |
| 5,720,751 A | 2/1998 | Jackson |
| 5,733,285 A | 3/1998 | Errico et al. |
| 5,752,957 A | 5/1998 | Ralph et al. |
| 5,810,818 A | 9/1998 | Errico et al. |
| 5,863,293 A | 1/1999 | Richelsoph |
| 5,964,760 A | 10/1999 | Richelsoph |
| 6,010,503 A | 1/2000 | Richelsoph et al. |
| 6,050,997 A | 4/2000 | Mullane |
| 6,077,262 A | 6/2000 | Schlapfer et al. |
| 6,086,588 A | 7/2000 | Ameil et al. |
| 6,132,432 A | 10/2000 | Richelsoph |
| 6,280,443 B1 | 8/2001 | Gu et al. |
| 6,296,642 B1 | 10/2001 | Morrison et al. |
| 6,302,888 B1 | 10/2001 | Mellinger et al. |
| 6,352,537 B1 | 3/2002 | Strnad |
| 6,485,491 B1 | 11/2002 | Farris et al. |
| 6,530,929 B1 | 3/2003 | Justis et al. |
| 6,858,030 B2 | 2/2005 | Martin et al. |
| 6,932,817 B2 | 8/2005 | Baynham et al. |
| 6,945,972 B2 | 9/2005 | Frigg et al. |
| 7,008,422 B2 | 3/2006 | Foley et al. |
| 7,160,300 B2 | 1/2007 | Jackson |
| 7,179,261 B2 | 2/2007 | Sicvol et al. |
| 7,207,992 B2 | 4/2007 | Ritland |
| 7,371,239 B2 | 5/2008 | Dec et al. |
| 7,465,306 B2 | 12/2008 | Pond et al. |
| 7,520,879 B2 | 4/2009 | Justis et al. |
| 7,572,281 B2 | 8/2009 | Runco et al. |
| 7,588,575 B2 | 9/2009 | Colleran et al. |
| 7,588,588 B2 | 9/2009 | Spitler et al. |
| 7,597,694 B2 | 10/2009 | Lim et al. |
| 7,608,095 B2 | 10/2009 | Yuan et al. |
| 7,611,517 B2 | 11/2009 | Lim |
| 7,618,442 B2 | 11/2009 | Spitler et al. |
| 7,621,916 B2 | 11/2009 | Lauryssen et al. |
| 7,621,918 B2 | 11/2009 | Jackson et al. |
| 7,625,376 B2 | 12/2009 | Brumfield et al. |
| 7,666,189 B2 * | 2/2010 | Gerber ............ A61B 17/7074 |
| | | | 606/104 |
| 7,666,210 B2 | 2/2010 | Franck et al. |
| 7,678,137 B2 | 3/2010 | Butler et al. |
| 7,682,377 B2 | 3/2010 | Konieczynski et al. |
| 7,686,835 B2 | 3/2010 | Warnick |
| 7,695,497 B2 | 4/2010 | Cordaro et al. |
| 7,695,498 B2 | 4/2010 | Ritland |
| 7,695,500 B2 | 4/2010 | Markworth |
| 7,699,872 B2 | 4/2010 | Farris et al. |
| 7,727,262 B2 | 6/2010 | Shaolian et al. |
| 7,744,598 B2 | 6/2010 | Brumfield et al. |
| 7,753,939 B2 | 7/2010 | Ritland |
| 7,758,584 B2 | 7/2010 | Bankoski et al. |
| 7,766,915 B2 | 8/2010 | Jackson |
| 7,780,703 B2 | 8/2010 | Yuan et al. |
| 7,824,411 B2 | 11/2010 | Varieur et al. |
| 7,824,413 B2 | 11/2010 | Varieur et al. |
| 7,854,751 B2 | 12/2010 | Sicvol et al. |
| 7,862,586 B2 | 1/2011 | Malek |
| 7,862,587 B2 | 1/2011 | Jackson et al. |
| 7,887,539 B2 | 2/2011 | Dunbar et al. |
| 7,887,541 B2 | 2/2011 | Runco et al. |
| 7,901,436 B2 | 3/2011 | Baccelli |
| 7,918,857 B2 | 4/2011 | Dziedzic et al. |
| 7,918,858 B2 | 4/2011 | Stad et al. |
| 7,918,878 B2 | 4/2011 | Sponger et al. |
| 7,922,727 B2 | 4/2011 | Songer et al. |
| 7,922,731 B2 | 4/2011 | Schumacher et al. |
| 7,927,334 B2 | 4/2011 | Miller et al. |
| 7,927,360 B2 | 4/2011 | Pond et al. |
| 7,942,901 B2 | 5/2011 | Rezach |
| 7,985,245 B2 | 7/2011 | Ritland |
| 7,988,698 B2 | 8/2011 | Rosenberg et al. |
| 7,998,144 B2 | 8/2011 | Schumacher et al. |
| 8,002,798 B2 | 8/2011 | Chin et al. |
| 8,002,804 B2 | 8/2011 | Lim et al. |
| 8,012,188 B2 | 9/2011 | Melkent et al. |
| 8,016,866 B2 | 9/2011 | Warnick |
| 8,062,340 B2 | 11/2011 | Berrevoets et al. |
| 8,066,739 B2 | 11/2011 | Jackson |
| 8,075,591 B2 | 12/2011 | Ludwig et al. |
| 8,096,996 B2 | 1/2012 | Gutierrez et al. |
| 8,100,915 B2 | 1/2012 | Jackson |
| 8,100,946 B2 | 1/2012 | Strausbaugh et al. |
| 8,100,951 B2 | 1/2012 | Justis et al. |
| 8,118,837 B2 | 2/2012 | Lemoine |
| 8,123,749 B2 | 2/2012 | Serhan et al. |
| 8,152,810 B2 | 4/2012 | Jackson |
| 8,162,948 B2 | 4/2012 | Jackson |
| 8,162,952 B2 | 4/2012 | Cohen et al. |
| 8,167,912 B2 | 5/2012 | Jacofsky et al. |
| 8,172,847 B2 | 5/2012 | Dziedzic et al. |
| 8,172,876 B2 | 5/2012 | Janowski et al. |
| 8,192,439 B2 | 6/2012 | Songer et al. |
| 8,197,519 B2 | 6/2012 | Schlaepfer et al. |
| 8,216,241 B2 | 7/2012 | Runco et al. |
| 8,235,997 B2 | 8/2012 | Hoffman et al. |
| 8,236,028 B2 | 8/2012 | Kalfas et al. |
| 8,257,399 B2 | 9/2012 | Biedermann et al. |
| 8,273,089 B2 | 9/2012 | Jackson |
| 8,287,546 B2 | 10/2012 | King et al. |
| 8,377,067 B2 | 2/2013 | Jackson |
| 8,394,133 B2 | 3/2013 | Jackson |
| 8,414,588 B2 | 4/2013 | Stad et al. |
| 8,419,773 B2 | 4/2013 | Biedermann et al. |
| 8,430,929 B2 | 4/2013 | Tribus |
| 8,444,649 B2 | 5/2013 | Stad et al. |
| 8,469,690 B2 | 6/2013 | Augustine |
| 8,518,082 B2 | 8/2013 | Sicvol et al. |
| 8,556,903 B2 | 10/2013 | Miller et al. |
| 8,591,515 B2 | 11/2013 | Jackson |
| 8,608,746 B2 | 12/2013 | Kold et al. |
| 8,617,210 B2 | 12/2013 | Sicvol et al. |
| 8,663,292 B2 | 3/2014 | Dec et al. |
| 8,679,128 B2 | 3/2014 | Seelig et al. |
| 8,721,685 B2 | 5/2014 | Foley et al. |
| 8,727,972 B2 | 5/2014 | Zhang et al. |
| 8,790,348 B2 | 7/2014 | Stad et al. |
| 8,870,890 B2 | 10/2014 | Aschmann et al. |
| 8,876,874 B2 | 11/2014 | Abdou et al. |
| 8,894,657 B2 | 11/2014 | Jackson |
| 8,900,237 B2 | 12/2014 | Ramsay et al. |
| 8,900,272 B2 | 12/2014 | Jackson |
| 8,961,524 B2 | 2/2015 | Foley et al. |
| 8,998,958 B2 | 4/2015 | Dauster et al. |
| 9,011,499 B1 * | 4/2015 | Kiester ............ A61B 17/7016 |
| | | | 606/246 |
| 9,055,978 B2 | 6/2015 | Jackson |
| 9,066,758 B2 * | 6/2015 | Justis ................ A61B 17/7032 |
| 9,101,415 B2 | 8/2015 | Jackson |
| 9,101,416 B2 | 8/2015 | Dunbar et al. |
| 9,173,682 B2 | 11/2015 | Jackson |
| 9,211,150 B2 | 12/2015 | Jackson |
| 9,216,039 B2 | 12/2015 | Jackson |
| 9,265,534 B2 | 2/2016 | Jackson |
| 9,265,535 B2 | 2/2016 | Jackson |
| 9,265,536 B2 | 2/2016 | Jackson |
| 9,265,537 B2 | 2/2016 | Jackson |
| 9,271,767 B2 | 3/2016 | Jackson |
| 2004/0111088 A1 | 6/2004 | Picetti et al. |
| 2004/0162558 A1 | 8/2004 | Hedge et al. |
| 2004/0186473 A1 | 9/2004 | Cournoyer et al. |
| 2005/0080415 A1 | 4/2005 | Keyer et al. |
| 2005/0245937 A1 | 11/2005 | Winslow et al. |
| 2005/0251141 A1 | 11/2005 | Frigg et al. |
| 2006/0084990 A1 | 4/2006 | Gournay et al. |
| 2006/0184178 A1 | 8/2006 | Jackson |
| 2006/0206114 A1 | 9/2006 | Ensign et al. |

(56) References Cited

U.S. PATENT DOCUMENTS

| | | |
|---|---|---|
| 2006/0293680 A1 | 12/2006 | Jackson |
| 2006/0293692 A1 | 12/2006 | Whipple et al. |
| 2007/0016200 A1 | 1/2007 | Jackson |
| 2007/0129731 A1 | 6/2007 | Sicvol et al. |
| 2007/0173825 A1 | 7/2007 | Sharifi-mehr et al. |
| 2007/0191842 A1 | 8/2007 | Molz et al. |
| 2007/0270817 A1 | 11/2007 | Rezach |
| 2007/0270842 A1* | 11/2007 | Bankoski ............ A61B 17/7076 606/86 A |
| 2008/0051780 A1 | 2/2008 | Vaidya et al. |
| 2008/0051787 A1 | 2/2008 | Remington et al. |
| 2008/0234757 A1 | 9/2008 | Jacofsky et al. |
| 2008/0294198 A1 | 11/2008 | Jackson |
| 2009/0204155 A1 | 8/2009 | Aschmann |
| 2009/0234395 A1* | 9/2009 | Hoffman ............ A61B 17/8875 606/86 A |
| 2009/0275992 A1 | 11/2009 | Phan et al. |
| 2009/0281582 A1 | 11/2009 | Villa et al. |
| 2009/0318970 A1 | 12/2009 | Butler et al. |
| 2010/0010542 A1 | 1/2010 | Jackson et al. |
| 2010/0094291 A1 | 4/2010 | Delbello |
| 2010/0114167 A1 | 5/2010 | Wilcox et al. |
| 2010/0131016 A1 | 5/2010 | Gerber et al. |
| 2010/0174319 A1 | 7/2010 | Jackson et al. |
| 2010/0331887 A1 | 12/2010 | Jackson et al. |
| 2011/0022093 A1* | 1/2011 | Sherman ............ A61B 17/7031 606/254 |
| 2012/0029568 A1 | 2/2012 | Jackson et al. |
| 2012/0035663 A1 | 2/2012 | Jackson |
| 2012/0277800 A1 | 11/2012 | Jackson |
| 2013/0018419 A1* | 1/2013 | Rezach ............ A61B 17/7076 606/264 |
| 2013/0296949 A1 | 11/2013 | Sicvol et al. |
| 2014/0222090 A1 | 8/2014 | Jackson |
| 2014/0379030 A1 | 12/2014 | Jackson |
| 2015/0080974 A1 | 3/2015 | Jackson |
| 2015/0182258 A1 | 7/2015 | Jackson |

* cited by examiner

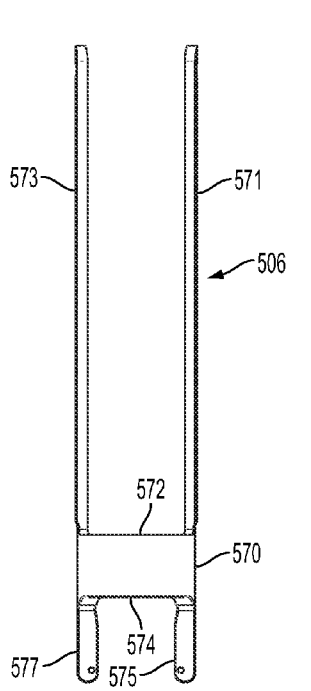
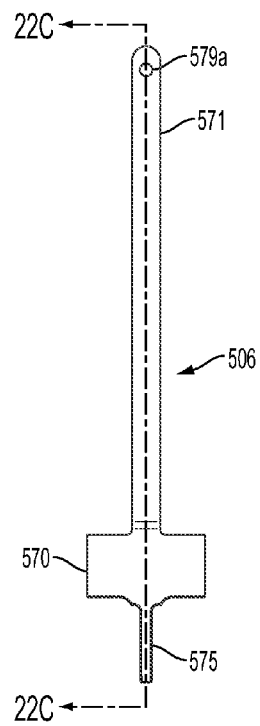
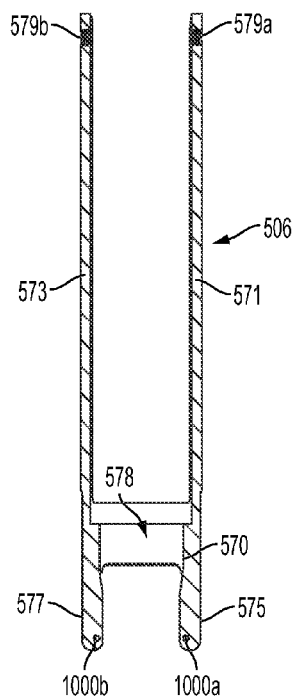
FIG. 22A　　FIG. 22B　　FIG. 22C
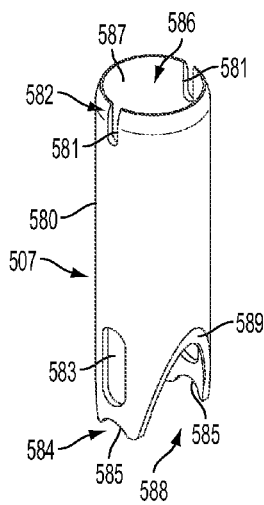
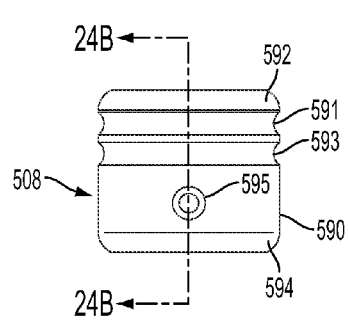
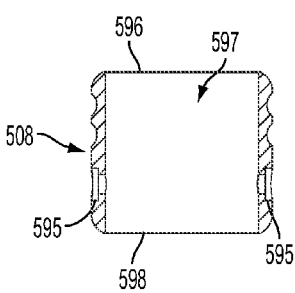
FIG. 23　　FIG. 24A　　FIG. 24B

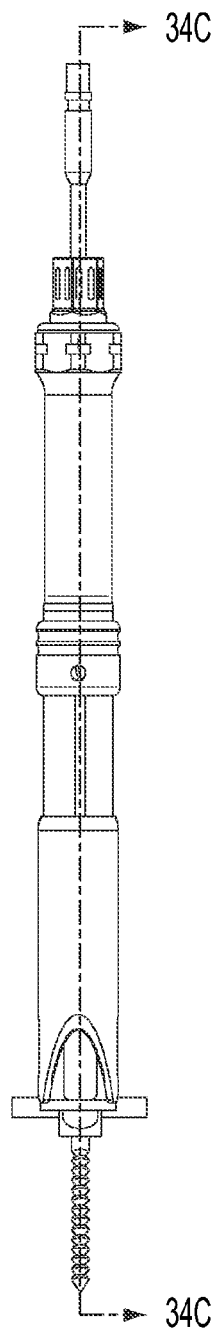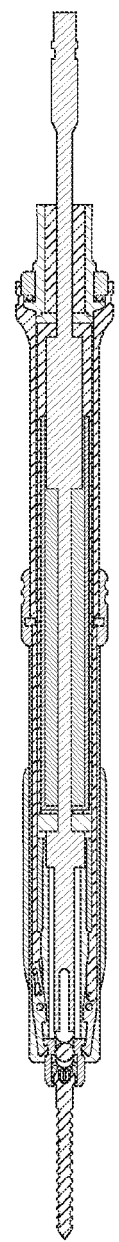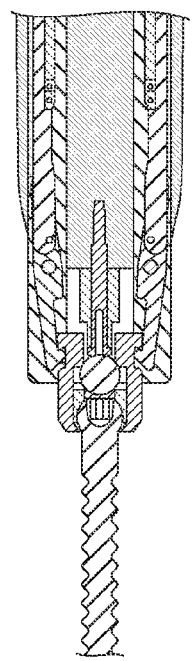
FIG. 34C
FIG. 34B
FIG. 34A

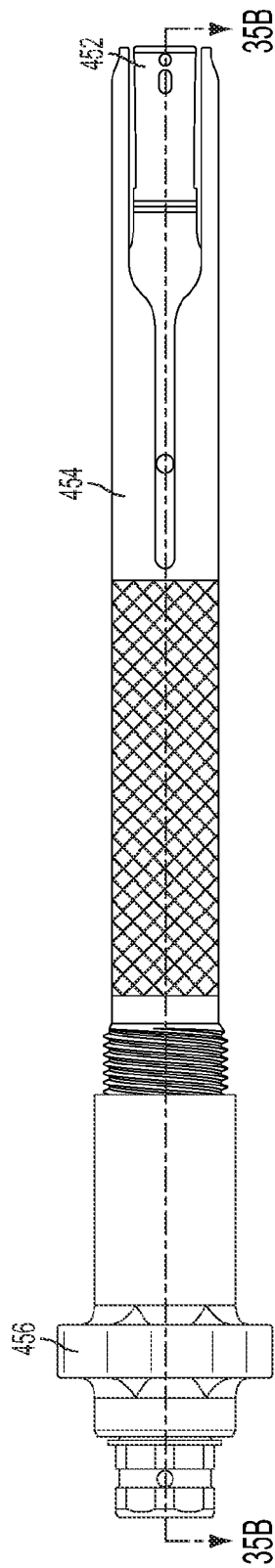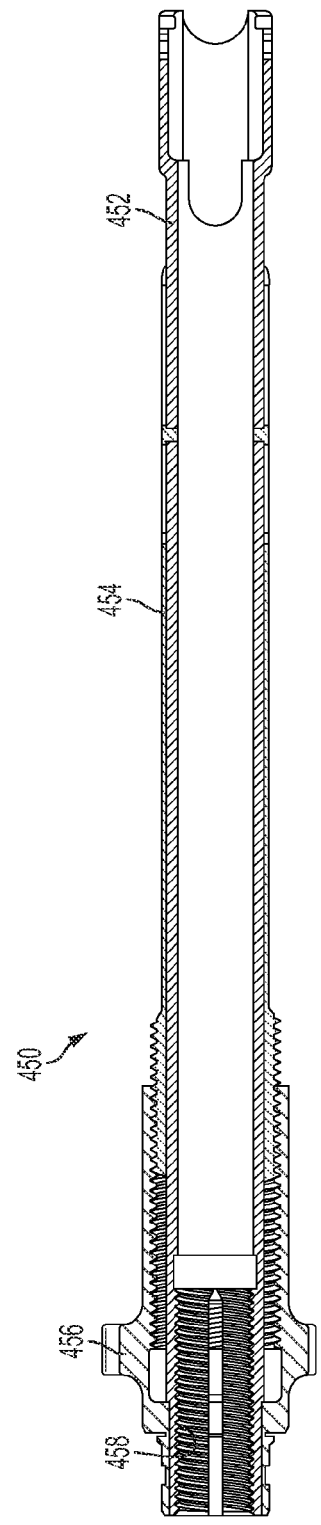
FIG. 35A
FIG. 35B

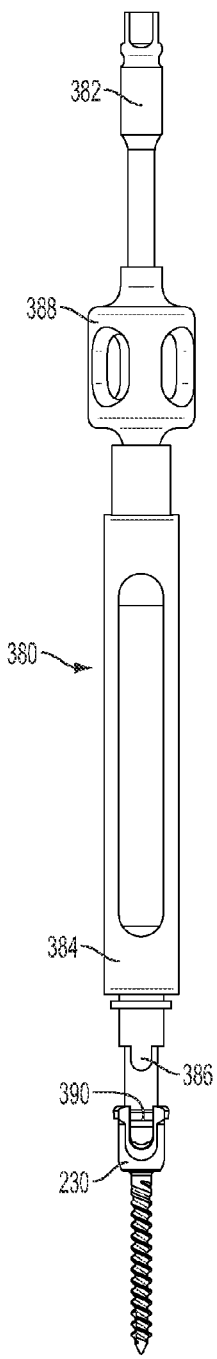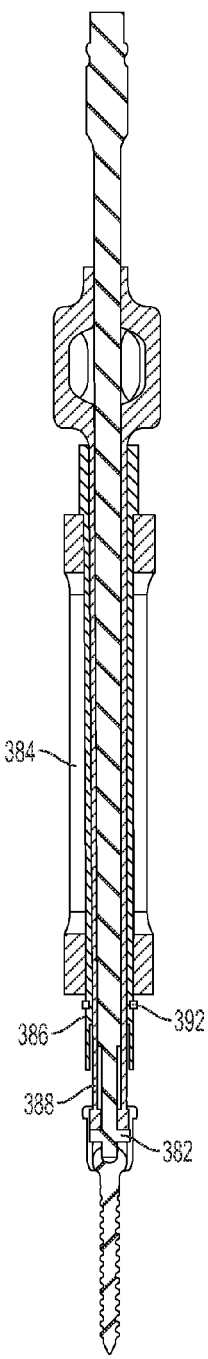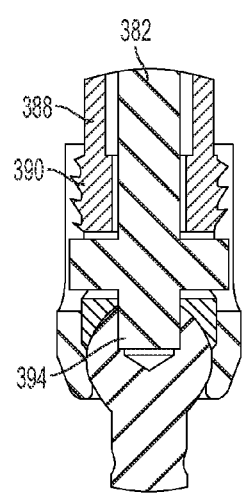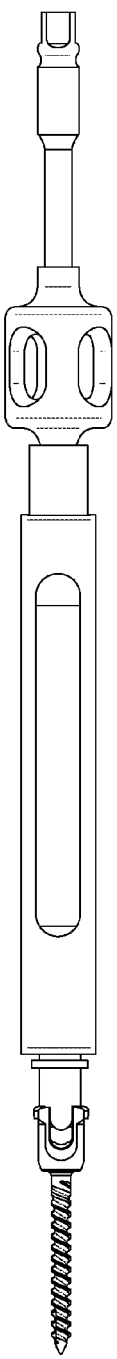
FIG. 37A    FIG. 37B    FIG. 38

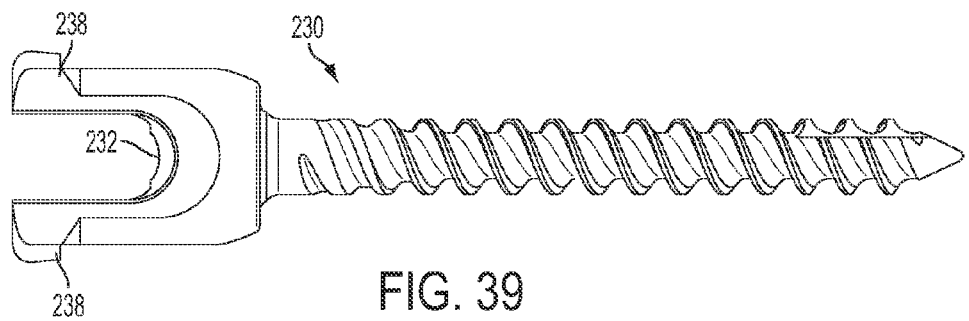
FIG. 39
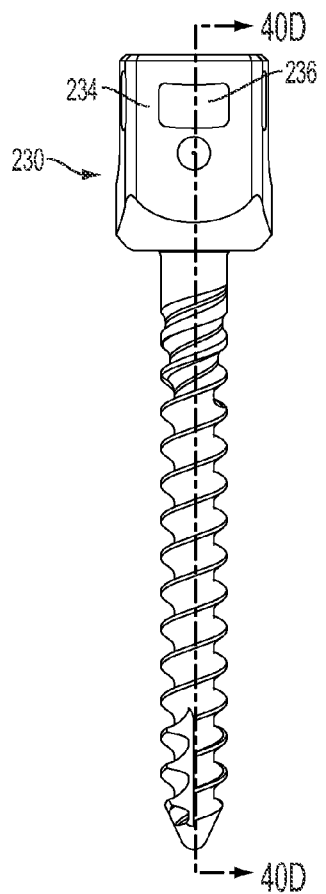
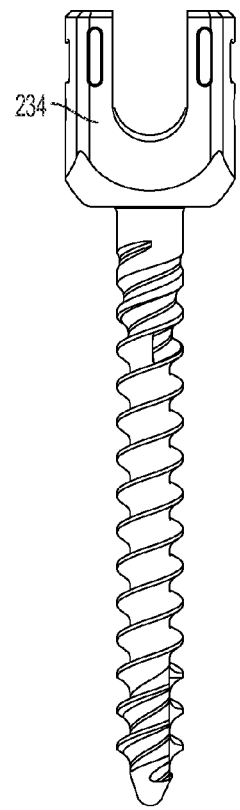
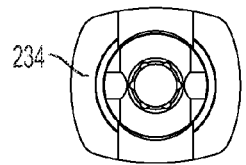
FIG. 40C
FIG. 40A   FIG. 40B
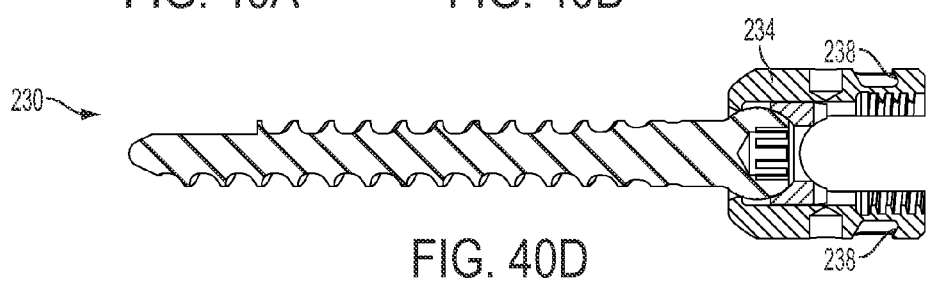
FIG. 40D

SURGICAL CONNECTORS AND INSTRUMENTATION

CROSS-REFERENCE TO RELATED APPLICATIONS

This application claims priority to U.S. Provisional Application Ser. No. 61/646,030 filed May 11, 2012 and U.S. Provisional Application Ser. No. 61/798,414 filed Mar. 15, 2013, which are incorporated by reference herein in their entirety.

TECHNICAL FIELD

The present disclosure relates to a system and technique for spinal surgery. Spinal implants, including connectors, hooks, screws and rods, are used to correct spinal deformities. Screws and connectors in combination with spinal rods can align and correct deformities in the natural spinal alignment as well as repair traumatic injury. Additionally, instrumentation for reduction of spinal rods into spinal pedicle screws is provided in the present disclosure.

BACKGROUND

Spinal fixation systems may be used in surgery to fix, adjust, and/or align the spinal column. One type of spinal fixation system employs a spinal rod for supporting the spine and fixing, adjusting, and/or aligning the spinal column into the desired orientation. Attachment of the spinal rod to the spinal column has been achieved using a variety of vertebral anchors. Vertebral anchors include screws, hooks, pins, and bolts used to engage the vertebrae and connect the spinal rod to different vertebrae.

The length and diameter of the spinal rod depends on the size and number of vertebrae to be held in a desired position by the spinal fixation system. The size of the spinal rod also depends on the region of the spine where the spinal fixation system is used. For example, in the cervical region of the spine, where the vertebrae tend to be smaller, a relatively smaller spinal rod is used. Conversely, in the thoracic region, where heavier loads are experienced and the vertebrae tend to be larger, a spinal rod having a relatively larger diameter is used. The cervico-thoracic junction of the spine is typically instrumented using spinal rods of two different diameters to accommodate anatomical differences between the cervical and thoracic spine regions. To accommodate a spinal fixation system including spinal rods having different sizes and configurations, a rod connector may be used to join a first spinal rod and a second spinal rod together. The rod connector may be a side-by-side connector, where the ends of the two spinal rods are placed side-by-side and connected using a connector that spans the two ends, or an axial connector, which aligns the axes of the two spinal rods and connects the ends of the spinal rods together along the axial direction. The plurality of possible spinal rod diameters in combination with the plurality of connector arrangements results in a surgeon typically requiring a vast array of connectors on hand in preparation for a given spinal surgery.

The spinal rods in a spinal fixation system may necessarily be bent to conform to a desired curvature of the spinal column in one or more of the anatomic planes as part of a spinal fixation or corrective surgery. Attachment of spinal rods to vertebral anchors such as screws, hooks, pins, and bolts may be complicated by differing curvature of the untreated spine and the curvature of the spinal rod. Instrumentation to force the spinal rod into engagement with the vertebral anchors may be used. Challenges arise in utilizing instrumentation to force the spinal rod into engagement with the vertebral anchors because the instrumentation generally must be releasably affixed to a previously implanted vertebral anchor and the locking mechanism on the vertebral anchor must be engaged while maintaining the spinal rod in the correct position. Simple engagement of the instrumentation with the vertebral anchor is desirable.

SUMMARY

In one embodiment, a medical device having a spinal rod receiving channel and a rod retaining set screw is provided. The spinal rod receiving channel has at least a first circular hole, a second circular hole, and a third circular hole overlapping in parallel arrangement. The first circular hole, the second circular hole, and the third circular hole have offset centers disposed along a single line. The first circular hole forms an upper arc of the rod receiving channel; the second circular hole forms a middle arc of the rod receiving channel; the third circular hole forms a lower arc of the rod receiving channel; and the middle arc and the lower arc are connected by a connecting slant. The rod retaining set screw secures a spinal rod disposed in the spinal rod receiving channel into the medical device.

In another embodiment, a medical device having a plurality of spinal rod receiving channel and a plurality of retaining set screw is provided. The spinal rod receiving channels each have at least a first circular hole, a second circular hole, and a third circular hole overlapping in parallel arrangement. The first circular hole, the second circular hole, and the third circular hole have offset centers disposed along a single line. The first circular hole forms an upper arc of the rod receiving channel; the second circular hole forms a middle arc of the rod receiving channel; the third circular hole forms a lower arc of the rod receiving channel; and the middle arc and the lower arc are connected by a connecting slant. The rod retaining set screws secures a spinal rod disposed in each of the spinal rod receiving channels into the medical device.

In another embodiment, a medical device having a spinal rod receiving channel, a rod retaining set screw, and a hook for engagement with the lamina of a vertebrae is provided. The spinal rod receiving channel has at least a first circular hole, a second circular hole, and a third circular hole overlapping in parallel arrangement. The first circular hole, the second circular hole, and the third circular hole have offset centers disposed along a single line. The first circular hole forms an upper arc of the rod receiving channel; the second circular hole forms a middle arc of the rod receiving channel; the third circular hole forms a lower arc of the rod receiving channel; and the middle arc and the lower arc are connected by a connecting slant. The rod retaining set screw secures a spinal rod disposed in the spinal rod receiving channel into the medical device.

In another embodiment, a medical device having a spinal rod receiving channel, a rod retaining set screw, and a lateral connector rod with a diameter of approximately 4.75 mm or 5.5 mm for engagement with a spinal pedicle screw is provided. The spinal rod receiving channel has at least a first circular hole, a second circular hole, and a third circular hole overlapping in parallel arrangement. The first circular hole, the second circular hole, and the third circular hole have offset centers disposed along a single line. The first circular hole forms an upper arc of the rod receiving channel; the second circular hole forms a middle arc of the rod receiving channel; the third circular hole forms a lower arc of the rod receiving channel; and the middle arc and the lower arc are connected by a connecting slant. The rod retaining set screw secures a spinal rod disposed in the spinal rod receiving channel into the medical device.

A another embodiment, a medical device having a first cross connector rod hook and a second cross connector hook for securing spinal rods, two conical screw receiving ports, and two rod retaining conical screws is provided. The first and second cross connector rod hooks have at least a first circular bore, a second circular bore, and a third circular bore which in combination form a hook with an open portion. The first circular bore, the second circular bore, and the third circular bore are parallel and have offset centers disposed along a single line. The first circular bore forms an upper arc of the cross connector rod hook; the second circular bore forms a middle arc of the cross connector rod hook; the third circular hole forms a lower arc of the cross connector rod hook; and the middle arc and the lower arc are connected by a connecting slant. The rod retaining conical screws secure a spinal rod disposed in the first and second cross connector rod hooks into the medical device.

In another embodiment, a medical device having a first cross connector rod hook and a second cross connector hook for securing spinal rods, two conical screw receiving ports, and two rod retaining conical screws is provided. The first and second cross connector rod hooks have at least a first circular bore, a second circular bore, and a third circular bore which in combination form a hook with an open portion. The first circular bore, the second circular bore, and the third circular bore are parallel and have offset centers disposed along a single line. The first circular bore forms an upper arc of the cross connector rod hook; the second circular bore forms a middle arc of the cross connector rod hook; the third circular hole forms a lower arc of the cross connector rod hook; and the middle arc and the lower arc are connected by a connecting slant. The rod retaining conical screws secure a spinal rod disposed in the first and second cross connector rod hooks into the medical device. The medical device further has a first linkage, a second linkage, a pivot post, and a midline nut. The first linkage comprises the first cross connector hook, one of the conical screw receiving ports and a bi-axial cross connector extension rod. The second linkage comprises the second cross connector hook, one of the conical screw receiving ports and a bi-axial cross connector. When assembled the bi-axial cross connector extension rod is disposed in the bi-axial cross connector extension rod channel, the linkage retaining orifice is disposed over the threaded post, and the midline nut is disposed on the threaded post.

In another embodiment, a medical instrument having a rod reduction assembly and a pedicle screw engaging assembly is provided. The rod reduction assembly comprises a rod reduction sleeve, a reduction rod, and an advancing knob. The reduction sleeve comprises a hollow, cylindrical shaped body having an internal reduction sleeve channel, reduction rod engagement slots on a first end, and rod engagement radii on a second end. The reduction rod comprises external reduction rod threads on a first end and the advancing knob comprises internal threads matched to the external reduction rod threads. The reduction rod has first and second extenders extending radial from the outer surface proximal a second end which engage with the reduction rod engagement slots. The pedicle screw engaging assembly has fingers for engagement with the head of a pedicle screw, finger cam pins, an inner tube, and a release ring. The fingers each comprise a finger hook having a finger hook undercut, a finger slot, and a finger aperture. The finger slot have a first end distal the finger hook with a width sufficient to permit finger cam pin to slide through but not enough for substantial lateral movement transverse to the sliding direction and a second end proximal the finger hook with a larger width to form a clearance fit with the finger cam pin. The inner tube comprises a hollow, cylindrical body having a first inner tube end and a second inner tube end, a first inner tube slot and a second inner tube slot diametrically opposed across the cylindrical body, and a first finger slot and a second finger slot diametrically opposed across the cylindrical body. The first inner tube slot and the second inner tube slot are open toward the second inner tube end and the fingers are disposed in the first finger slot and the second finger slot with the fingers oriented to dispose the finger hooks proximal the second inner tube end and the finger hook undercuts toward the interior of the inner tube. Movement of the release ring from a first position to a second position moves the finger cam pins from the second end of the finger slot to the first end of the finger slot thereby positioning the fingers for insertion of the head of a pedicle screw.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 22A is a front view of an embodiment of a retractor sleeve of a rod reduction device;

FIG. 22B is a side view of an embodiment of a retractor sleeve of a rod reduction device;

FIG. 22C is a front section view of an embodiment of a retractor sleeve of a rod reduction device;

FIG. 23 is an isometric view of an embodiment of a reduction sleeve of a rod reduction device;

FIG. 24A is a front view of an embodiment of a release ring of a rod reduction device;

FIG. 24B is a section view of an embodiment of a release ring of a rod reduction device;

FIG. 34A is a side view of an embodiment of a rod reduction device attached to a spinal pedicle screw, a spinal rod reduced into the spinal pedicle screw, and a rod retaining set screw inserted;

FIG. 34B is a section view of an embodiment of a rod reduction device attached to a spinal pedicle screw, a spinal rod reduced into the spinal pedicle screw, and a rod retaining set screw inserted;

FIG. 34C is a detail section view of an embodiment of a rod reduction device attached to a spinal pedicle screw, a spinal rod reduced into the spinal pedicle screw, and a rod retaining set screw inserted;

FIG. 35A is a front profile view of an embodiment of a rod reduction assembly;

FIG. 35B is a section view of an embodiment of a rod reduction assembly;

FIG. 37A is a front profile view of an embodiment of a spinal pedicle screw inserter;

FIG. 37B is a section view of an embodiment of a spinal pedicle screw inserter;

FIG. 37C is a detail section view of an embodiment of a spinal pedicle screw inserter;

FIG. 38 is a front profile view of an embodiment of a spinal pedicle screw inserter;

FIG. 39 is a front profile view of an embodiment of a spinal pedicle screw;

FIG. 40A is a side profile view of an embodiment of a spinal pedicle screw;

FIG. 40B is a front profile view of an embodiment of a spinal pedicle screw;

FIG. 40C is a top profile view of an embodiment of a spinal pedicle screw; and

FIG. 40D is a section view of an embodiment of a spinal pedicle screw.

DETAILED DESCRIPTION

Figure 1:
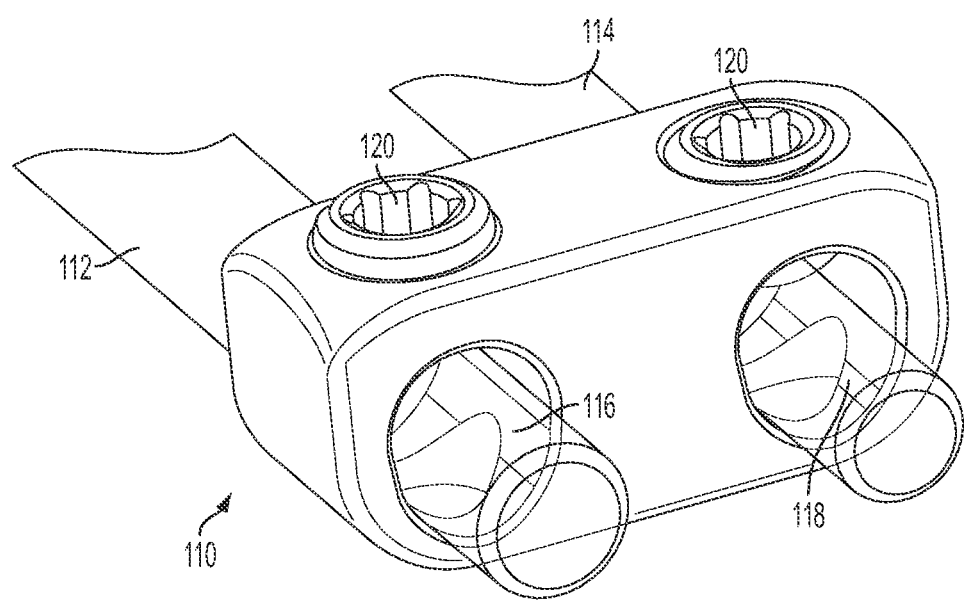
FIG. 1 is an isometric view of an embodiment of a dual diameter connector with rods disposed therein.

Referring initially to FIG. 1, an isometric view of a wedding band inline dual diameter connector 110 with spinal rods 112, 114 disposed therein. The wedding band inline dual diameter connector 110 illustrated in FIG. 1 specifically has a 5.5 mm diameter spinal rod 112 and a 4.75 mm diameter spinal rod 114 disposed therein.

The wedding band inline dual diameter connector 110 connects two spinal rods 112, 114 in a substantially parallel orientation. The wedding band inline dual diameter connector 110 allows a surgeon performing a spinal surgery to utilize multiple spinal rods 112, 114 along the length of the spine in lieu of a single long rod. Use of multiple spinal rods 112, 114 allows for different diameter spinal rods to be used along the length of the spine based on changes in anatomy. Changing diameters of spinal rods 112, 114 also allows for the mechanical properties, such as stiffness, of the fixation or deformity correction to be varied along the length of the patient's spine.

In addition to different sized spinal rods, multiple spinal rods of the same diameter may be connected together. For example, two 5.5 mm diameter spinal rods 112 may be joined. Additionally, two 4.75 mm diameter spinal rods 114 may be joined.

Figures 2A, 2B:
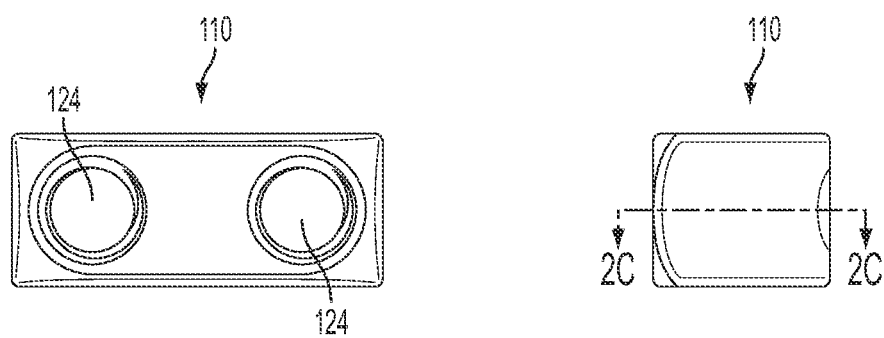
FIG. 2A is a top view of an embodiment of a dual diameter connector.
FIG. 2B is an end view of an embodiment of a dual diameter connector.
Figure 2C:
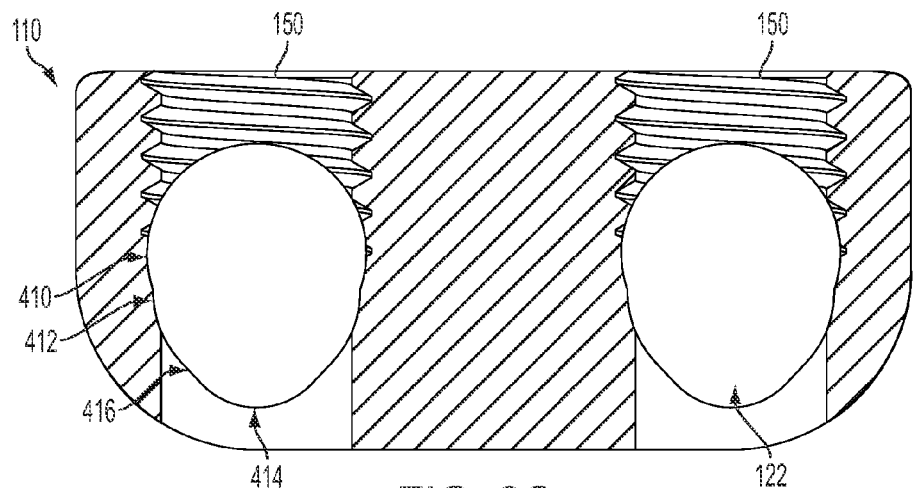
FIG. 2C is a front section view of an embodiment of a dual diameter connector.

Referring to FIGS. 2A-2C, an embodiment of a wedding band inline dual diameter connector 110, rod receiving channels 122 are shown. The specific and special geometry of the rod receiving channels 122 allows for both 5.5 mm diameter spinal rods 112 and 4.75 mm diameter spinal rods 114 to be secured in the rod receiving channels. The rod receiving channels 122 are substantially a composite of three circular through holes. The resulting rod receiving channel 122 is comprised of one upper arc 410, two middle arcs 412, two connecting slants 416, and one lower arc 414. The upper arc 410 preferably has an approximately 2.76 mm to approximately 3.02 mm radius. For example, a radius of 2.890 mm. The middle arc 412 preferably has an approximately 2.595 mm to approximately 2.855 mm radius. For example, a radius of 2.725 mm. The lower arc 414 preferably has an approximately 1.87 mm to approximately 2.13 mm radius. For example, a radius of 2.000 mm. The connecting slant 416 preferably has a length of approximately 0.638 mm to approximately 0.898 mm. For example, a length of 0.768 mm. The centers of the upper arc 410, the middle arc 412, and the lower arc 414 are co-linear. The center of the middle arc 412 is located between the center of the upper arc 410 and the lower arc 414. The centers of the upper arc 410 and middle arc 412 are preferably separated by approximately 1.00 mm to approximately 1.07 mm. The centers of the lower arc 414 and middle arc 412 are preferably separated by approximately 1.02 mm to approximately 1.09 mm. The angle of the connecting slant 416 is preferably approximately 42° to approximately 44° from the line formed by the centers of the upper arc 410, the middle arc 412, and the lower arc 414.

Set screw receiving ports 124 are positioned in alignment with the rod receiving channels 122. The set screw receiving ports 124 are configured to engage with a set screw 120 through threaded engagement. Set screw receiving threads 150 are positioned on the interior surface of the set screw receiving ports 124 to engage with external threads on set screw 120. Set screws 120 are threaded into the wedding band inline dual diameter connector 110 and abutted against the spinal rods 112, 114 to secure the spinal rods into the wedding band inline dual diameter connector.

In an embodiment of the wedding band inline dual diameter connector 110, a rod receiving channel relief 126 is disposed opposite each set screw receiving port 124. The rod receiving channel relief 126 in an embodiment is a circular through hole diametrically opposite the set screw receiving port 124.

Referring again to FIG. 1, the spinal rods 112, 114 are illustrated as translucent to allow the interface between the wedding band inline dual diameter connector 110 and the spinal rods to be seen. The 5.5 mm diameter spinal rod 112 contacts the wedding band inline dual diameter connector 110 in a 5.5 mm contact area 116 demarcated as a shaded region. The 4.75 mm diameter spinal rod 114 contacts the wedding band inline dual diameter connector 110 in a 4.75 mm contact area 118 demarcated as a second shaded region. Both the 5.5 mm contact area 116 and the 4.75 mm contact area 118 are mirrored on the opposing surface of the respective spinal rod 112, 114 and connector interface (not shown).

In a specific embodiment the 5.5 mm contact area 116 is approximately 32.08 mm$^2$ and the 4.75 mm contact area 118 is approximately 7.44 mm$^2$. These contact areas can vary according to the limits of the full range of disclosed embodiments of the rod receiving channels 122.

Figure 3A:
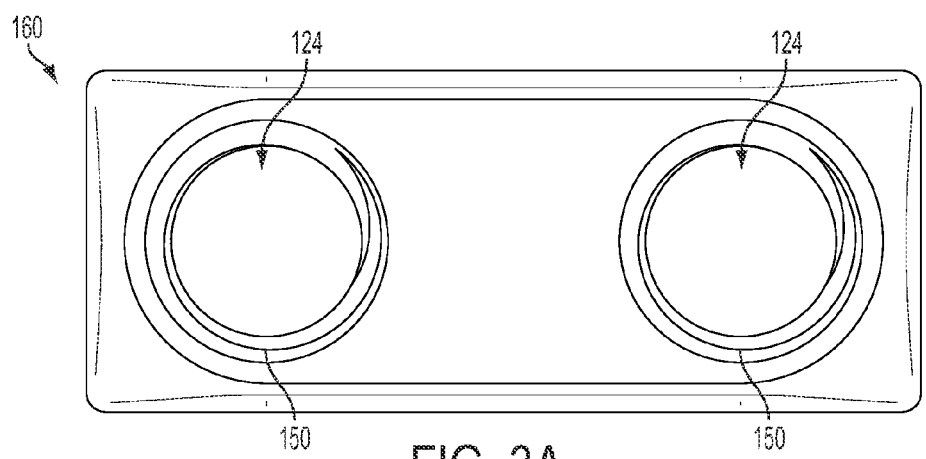
FIG. 3A is a top view of an embodiment of a dual diameter connector.
Figure 3B:
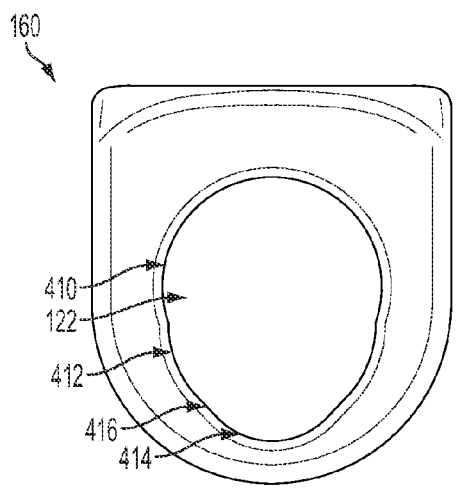
FIG. 3B is an end view of an embodiment of a dual diameter connector.

Referring to FIG. 3A and FIG. 3B, a top profile and end profile respectively of an inline dual diameter connector 160 is shown. The inline dual diameter connector 160 has the same closed rod receiving channel 122 profile as described for the wedding band inline dual diameter connector 110. In the inline dual diameter connector 160, a single closed rod receiving channel 122 passes along the entire longitudinal axis. This arrangement allows two spinal rods 112, 114 to be abutted end to end without any lateral shift required.

Figure 4:
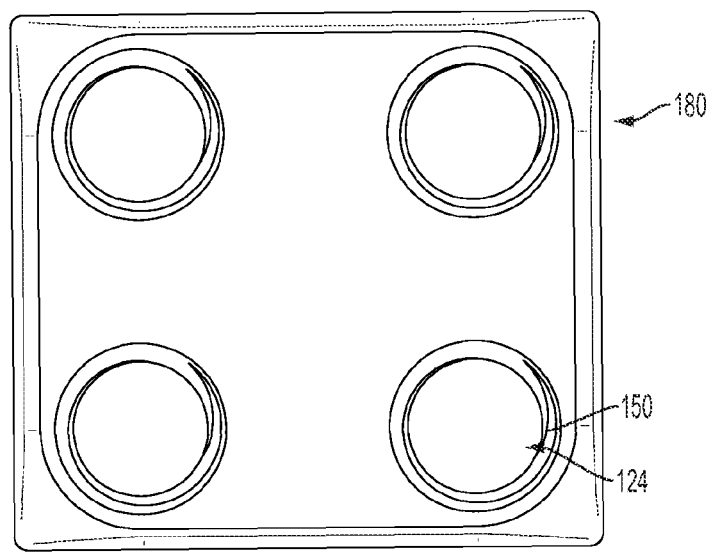
FIG. 4 is a top view of an embodiment of a dual diameter connector.

Referring to FIG. 4, a domino inline dual diameter connector 180 is shown in a top profile view. The domino inline dual diameter connector 180 also has a front profile matching that of the wedding band inline dual diameter connector 110 as shown in FIG. 2A and FIG. 2C. The arrangement of the domino inline dual diameter connector 180 is that of two inline dual diameter connectors 160 disposed side by side.

It is envisioned that four spinal rods 112, 114 can be secured together, wherein each single spinal rod is secured by an individual set screw 120 disposed in each of the four set screw receiving ports 124. It is also envisioned that two spinal rods 112, 114 can be secured in a parallel orientation with two set screws 120 securing each spinal rod. The domino inline dual diameter connector 180 may secure any combination of 4.75 mm diameter spinal rods 114 and 5.5 mm diameter spinal rods 112 at each of the set screw receiving ports 124. Non-limiting examples include two 4.75 mm diameter spinal rods 114 secured with two set screws 120 securing each rod, a single 4.75 mm diameter spinal rod 114 and a single 5.5 mm diameter spinal rod 112 with two set screws 120 securing each rod, two 4.75 mm diameter spinal rods 114 and two 5.5 mm diameter spinal rods 112 secured with one set screw 120 securing each rod, two 4.75 mm diameter spinal rods 114 and one 5.5 mm diameter spinal rod 112 secured with one set screw 120 securing each 4.75 mm diameter spinal rod and two set screws 120 securing the 5.5 mm diameter spinal rod, and two 5.5 mm diameter spinal rods 112 and one 4.75 mm diameter spinal rod 114 secured with one set screw 120 securing each 5.5 mm diameter spinal rod and two set screws 120 securing the 4.75 mm diameter spinal rod.

Figure 5A:
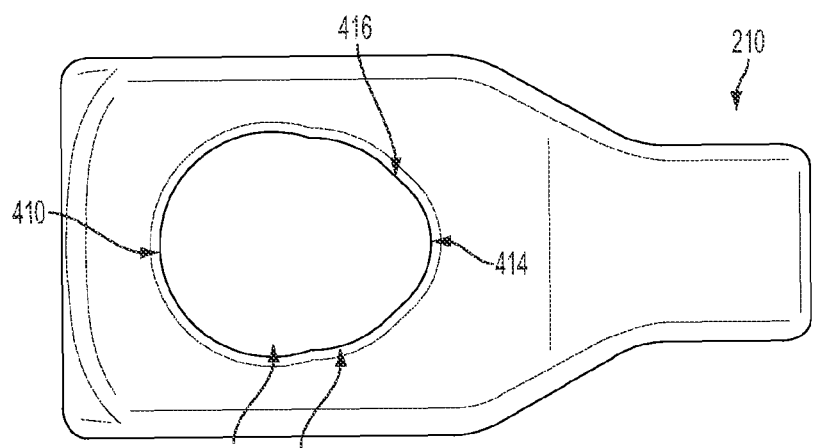
FIG. 5A is a front profile view of an embodiment of a dual diameter closed laminar hook.
Figure 5B:
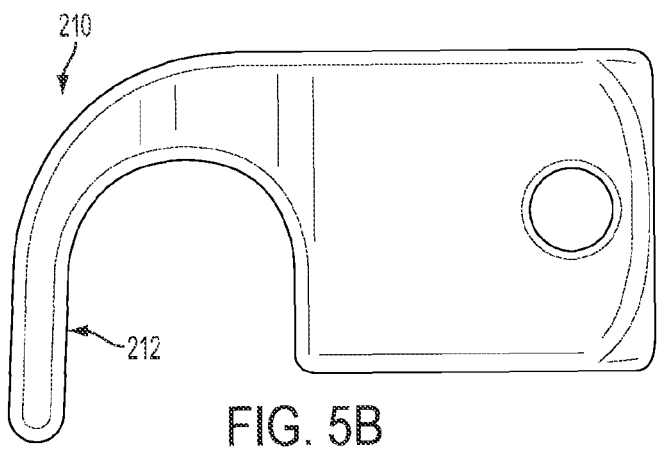
FIG. 5B is a side view of an embodiment of a dual diameter closed laminar hook.

Referring to FIG. 5A and FIG. 5B, a front profile view and a side profile view respectively of a closed laminar hook 210. The closed laminar hook 210 comprises a set screw receiving port 124, a closed rod receiving channel 122, and a hook blade 212. The hook blade 212 may be of varying widths and lengths.

Other standard styles and sizes of hooks are envisioned. Non-limiting examples include closed and open pedicle hooks, closed laminar hooks 210, open laminar hooks 220, open thoracic hooks, open offset thoracic hooks, and open offset lumbar hooks.

Figure 6:
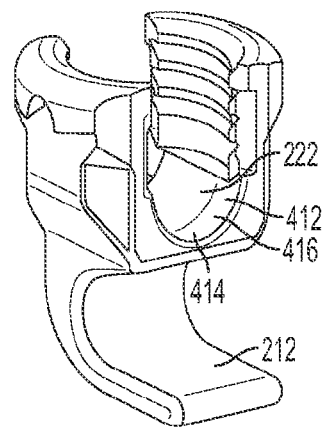
FIG. 6 is an isometric view of an embodiment of a dual diameter open laminar hook.

Referring to FIG. 6, an isometric view of an open laminar hook 220. The open laminar hook 220 comprises an open rod receiving saddle 222 and a hook blade 212. The hook blade 212 may be of varying widths and lengths.

The open rod receiving saddle 222 comprises the same geometry as closed rod receiving channel 122 except the upper arc 410 is not present and a portion of middle arc 412 may also be not present. In an embodiment, the upper threaded portion of the open laminar hook 220 may replicate the geometry of any uniaxial or polyaxial spinal screw known to one skilled in the art. Additionally, in an embodiment of the open laminar hook 220 the external geometry may replicate the external shape and geometry of any uniaxial or polyaxial spinal screw known to one skilled in the art.

Figure 7A:
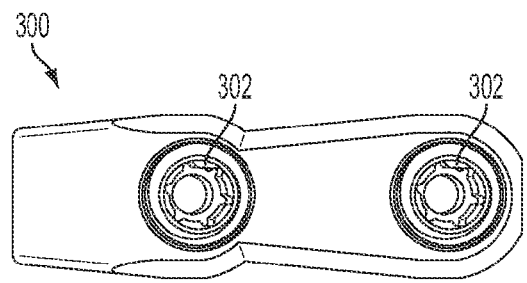
FIG. 7A is a top view of an embodiment of a dual diameter fixed cross connector.
Figure 7B:
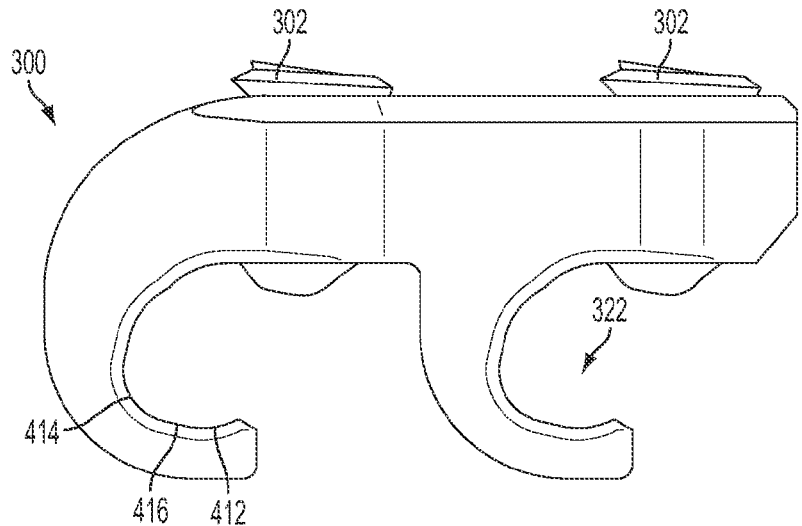
FIG. 7B is a front view of an embodiment of a dual diameter fixed cross connector.

Referring to FIG. 7A and FIG. 7B, a top and front view respectively of a fixed cross connector 300. The fixed cross connector 300 comprises a cross connector rod hook 322 and a conical screw 302 at each end. The conical screw 302 retains a spinal rod 112, 114 in the respective cross connector rod hook 322. The distance between the two cross connector rod hooks 322 may be varied to allow the fixed cross connector 300 to be attached to spinal rods 112, 114 at various lateral spacing. In selected embodiments the distance between the centers of the two cross connector rod hooks 322 is between approximately 10 mm and approximately 40 mm. In a further selected embodiment the distance between the centers of the two cross connector rod hooks 322 is between approximately 14 mm and approximately 36 mm. Non-limiting examples include a distance between the centers of the two cross connector rod hooks 322 of approximately 14 mm, approximately 16 mm, approximately 18 mm, approximately 20 mm, approximately 22 mm, approximately 24 mm, approximately 26 mm, approximately 28 mm, approximately 30 mm, approximately 32 mm, approximately 34 mm, and approximately 36 mm.

Figure 8:
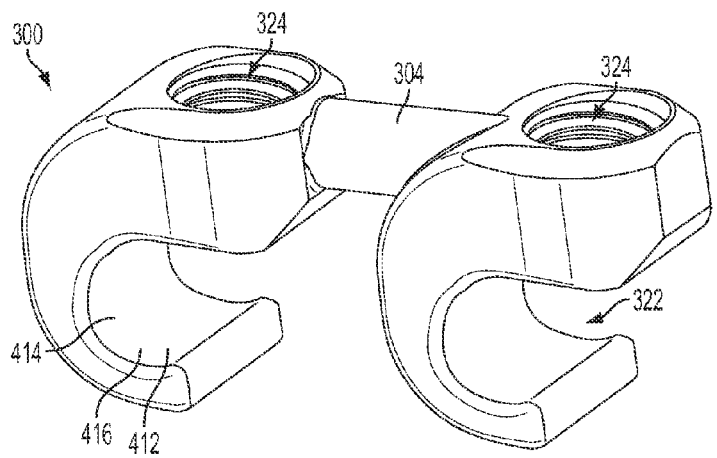
FIG. 8 is an isometric view of an embodiment of a dual diameter fixed cross connector.

Referring to FIG. 8, an isometric view of a further embodiment of the fixed cross connector 300. In this embodiment the ends of the fixed cross connector 300 are connected by a fixed cross connector extension rod 304. The fixed cross connector extension rod 304 may be of varying lengths to provide a fixed cross connector 300 configured to attach to spinal rods 112, 114 at various lateral spacing. In selected embodiments the distance between the centers of the two cross connector rod hooks 322 is between approximately 10 mm and approximately 40 mm. In a further selected embodiment the distance between the centers of the two cross connector rod hooks 322 is between approximately 14 mm and approximately 36 mm. Non-limiting examples include a distance between the centers of the two cross connector rod hooks 322 of approximately 14 mm, approximately 16 mm, approximately 18 mm, approximately 20 mm, approximately 22 mm, approximately 24 mm, approximately 26 mm, approximately 28 mm, approximately 30 mm, approximately 32 mm, approximately 34 mm, and approximately 36 mm. The fixed cross connector extension rod 304 may also be curved or angulated to allow fixation to spinal rods 112, 114 which are not in parallel alignment. The conical screw receiving port 324 accepts a conical screw 302 for securing a spinal rod 112, 114 in the respective cross connector rod hook 322.

Figure 9B:
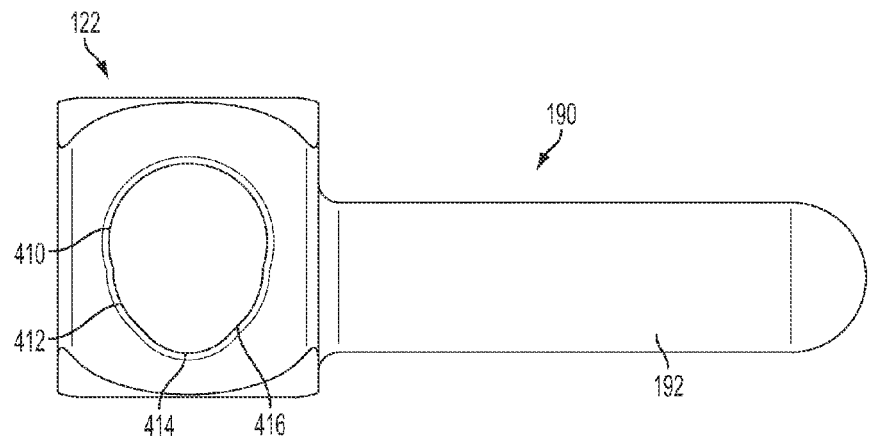
FIG. 9B is a front view of an embodiment of a dual diameter closed lateral connector.
Figures 9A, 9C:
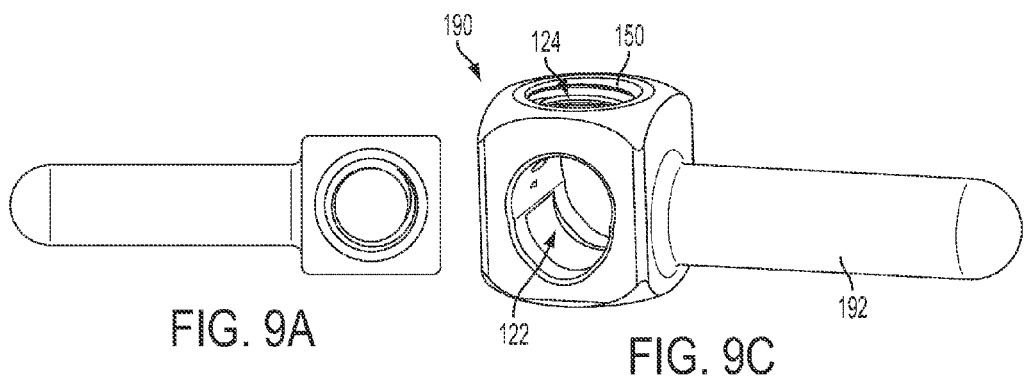
FIG. 9A is a top view of an embodiment of a dual diameter closed lateral connector.
FIG. 9C is an isometric view of an embodiment of a dual diameter closed lateral connector.

Referring to FIG. 9A, FIG. 9B, and FIG. 9C, a front profile, top profile, and an isometric view respectively of a closed lateral connector 190. The closed lateral connector 190 comprises a lateral connector rod 192, a set screw receiving port 124, and a closed rod receiving channel 122. The lateral connector 190 may be affixed to a polyaxial screw 230 [shown in FIG. 39] or a uniaxial screw with the lateral connector rod 192 disposed in the screw saddle 232. The lateral connector rod 192 is sized to match a standard spinal rod 112, 114. The lateral connector rod 192 is preferably circular and approximately 4.75 mm or approximately 5.5 mm in diameter. The lateral connector rod 192 may also be varying lengths. The lateral connector rod 192 is preferably approximately 15 mm to approximately 80 mm in length and more preferably approximately 20 mm to approximately 60 mm in length. Non-limiting examples include a lateral connector rod 192 with a length of approximately 20 mm, approximately 30 mm, approximately 40 mm, and approximately 60 mm.

Figure 10A:
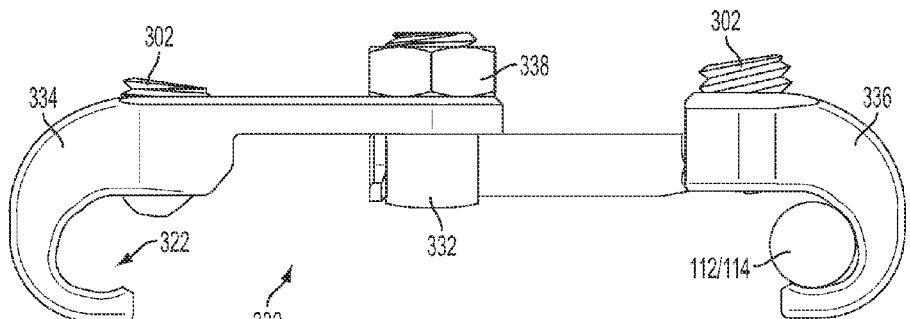
FIG. 10A is a front view of an embodiment of a dual diameter bi-axial cross connector.

Referring to FIG. 10A, a front profile view of a bi-axial cross connector 330. The bi-axial cross connector 330 comprises a first linkage 336, a second linkage 334, a pivot post 332, a midline nut 338, and a pair of conical screws 302. The first linkage 336 and the second linkage 334 can extend along a first axis to lengthen the bi-axial cross connector 330. Adjustment of the length along the first axis allows the bi-axial cross connector 330 to be affixed to spinal rods 112, 114 laterally spaced at any distance along a continuum. This is in contrast to a fixed cross connector 300, wherein the spinal rods must be laterally spaced at approximately one of a finite number of predetermined distances. The first linkage 336 and second linkage 334 may also rotate relative to each other about the first axis. Rotation of the first linkage 336 and second linkage 334 about the first axis allows the bi-axial cross connector 330 to be affixed to spinal rods 112, 114 which are skewed in the sagittal plane. The first linkage 336 and the second linkage 334 are also angulated about a second axis perpendicular to the first axis. Angulation of the first linkage 336 and the second linkage 334 about the second axis allows the bi-axial cross connector 330 to be affixed to spinal rods 112, 114 which are skewed in the coronal plane.

Adjustment of the length of the bi-axial cross connector 330 along the first axis allows the bi-axial cross connector 330 to be affixed to spinal rods 112, 114 laterally spaced at any distance along a continuum within predetermined ranges.

Figure 11A:
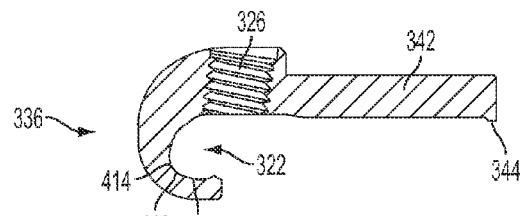
FIG. 11A is a front section view of an embodiment of a first linkage of an embodiment of a dual diameter bi-axial cross connector.
Figure 11B:
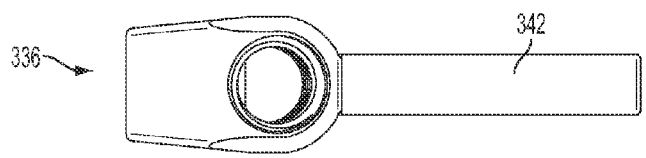
FIG. 11B is a top view of an embodiment of a first linkage of an embodiment of a dual diameter bi-axial cross connector.

Referring to FIGS. 11A and 11B, the first linkage 336 comprises a cross connector rod hook 322, a bi-axial cross connector extension rod 342, and a bi-axial cross connector extension rod limiter 344. Cross connector rod hook 322 comprises the same geometry as closed rod receiving channel 122 except the upper arc 410 is not present and a portion of middle arc 412 may also be not present. The bi-axial cross connector extension rod 342 is a round shaft with the bi-axial cross connector extension rod limiter 344 disposed on the end. The bi-axial cross connector extension rod limiter 344 helps prevent the bi-axial cross connector extension rod 342 from disengaging from the pivot post 332 during manipulation of the bi-axial cross connector 330. The bi-axial cross connector extension rod 342 is preferably approximately 10 mm to approximately 40 mm in length and more preferably approximately 17 mm to approximately 32 mm in length. The bi-axial cross connector extension rod 342 is preferably approximately 3.5 mm to approximately 4.5 mm in diameter and more preferably approximately 3.9 mm to approximately 4.1 mm in diameter. For example, the bi-axial cross connector extension rod 342 may be 24 mm in length and 3.98 mm in diameter.

Figure 12A:
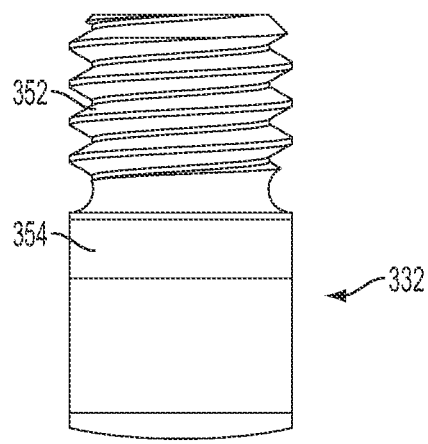
FIG. 12A is a side view of an embodiment of a pivot post of an embodiment of a dual diameter bi-axial cross connector.
Figure 12B:
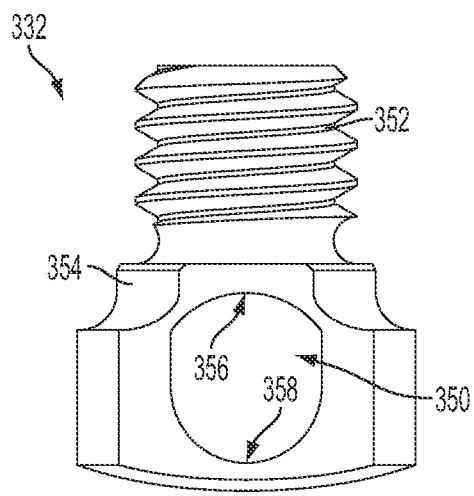
FIG. 12B is a front view of an embodiment of a pivot post of an embodiment of a dual diameter bi-axial cross connector.

Referring to FIG. 12A and FIG. 12B, a side profile and front profile respectively of the pivot post 332. The pivot post 332 comprises a bi-axial cross connector extension rod channel 350, a threaded post 352, and a linkage retaining shoulder 354. The bi-axial cross connector extension rod channel 350 is configured to allow the bi-axial cross connector extension rod 342 and the bi-axial cross connector extension rod limiter 344 to pass through unimpeded when the bi-axial cross connector extension rod is in contact with a first surface 356. Conversely, the bi-axial cross connector extension rod channel 350 is configured to prohibit the bi-axial cross connector extension rod 342 and the bi-axial cross connector extension rod limiter 344 to pass through unimpeded when the bi-axial cross connector extension rod is in contact with a second surface 358, as the bi-axial cross connector extension rod limiter catches on the pivot post 332. The threaded post 352 comprises threads configured to engage with internal threads on the midline nut 338.

The first surface 356 of the bi-axial cross connector extension rod channel 350 of the pivot post 332 preferably is an arc with a diameter of approximately 0.6 to approximately 1.4 mm larger than the diameter of the bi-axial cross connector extension rod 342. The second surface 358 of the bi-axial cross connector extension rod channel 350 of the pivot post 332 preferably is an arc with a diameter of approximately 0.03 to approximately 0.30 mm larger than the diameter of the bi-axial cross connector extension rod 342. For example, as in the previous example, the bi-axial cross connector extension rod 342 may be 3.98 mm in diameter and the diameter of the arc of the first surface 356 may be 4.98 mm and the diameter of the second surface 358 may be 4.02 mm.

Figure 13A:
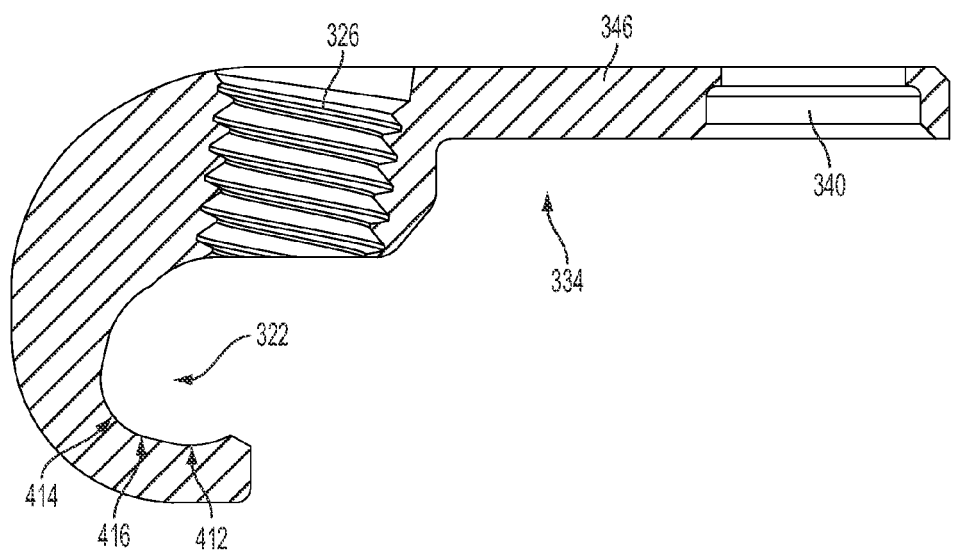
FIG. 13A is a front section view of an embodiment of a second linkage of an embodiment of a dual diameter bi-axial cross connector.
Figure 13B:
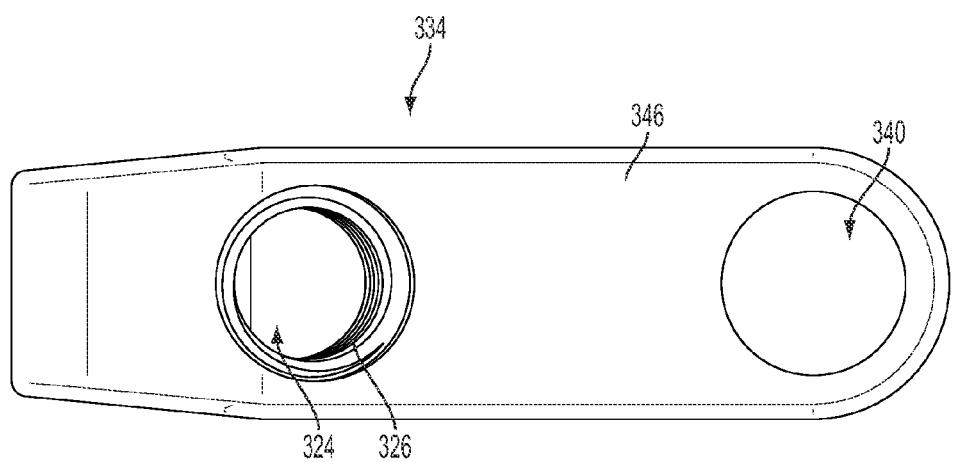
FIG. 13B is a top view of an embodiment of a second linkage of an embodiment of a dual diameter bi-axial cross connector.

Referring to FIG. 13A and FIG. 13B, a front profile view and a top profile view respectively of the second linkage 334. The second linkage 334 comprises a cross connector rod hook 322, a conical screw receiving port 324 with conical screw receiving threads 326, and a bi-axial cross connector extension plank 346 having a linkage retaining orifice 340. The linkage retaining orifice 340 engages with the linkage retaining shoulder 354 of the pivot post 332. The bi-axial cross connector extension plank 346 is a flat strip extending away from the conical screw receiving port 324 and cross connector rod hook 322. The bi-axial cross connector extension plank 346 is preferably approximately 10 mm to approximately 40 mm in length and more preferably approximately 17 mm to approximately 32 mm in length. The length of the bi-axial cross connector extension plank 346 is the length of the thinned portion of the second linkage 334. For example, the bi-axial cross connector extension plank 346 may be approximately 17 mm in length, approximately 18 mm in length, approximately 20 mm in length, approximately 24 mm in length, and approximately 32 mm in length.

When assembled, the midline nut 338 presses the second linkage 334 toward the linkage retaining shoulder 354 which in turn presses the second linkage into the bi-axial cross connector extension rod 342 which is passed through the bi-axial cross connector extension rod channel 350. The compressive force of the midline nut 338, in conjunction with frictional forces, prevent the bi-axial cross connector 330 from extending along the first axis, rotating about the first axis, or angulating about the second axis.

Referring again to FIG. 10A, a front profile of the bi-axial cross connector 330 in an extended configuration. The bi-axial cross connector 330 can secure both the 5.5 mm diameter spinal rod 112 and the 4.75 mm diameter spinal rod 114. The 5.5 mm diameter spinal rod 112 is shown in FIG. 10A in the cross connector rod hook 322 in an unsecured configuration as the conical screw 302 is not fully advanced and pressing the spinal rod into the cross connector rod hook.

Figure 10B:
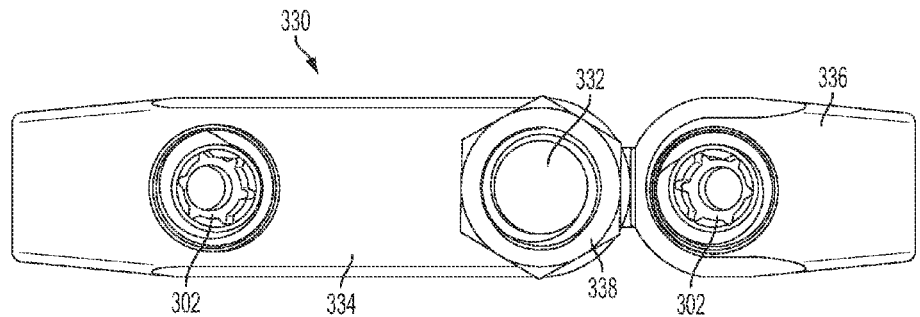
FIG. 10B is a top view of an embodiment of a dual diameter bi-axial cross connector.

Referring to FIG. 10B, a top profile of the bi-axial cross connector 330 in a retracted configuration. The conical screw 302 has a hexalobular internal driving feature.

In an embodiment of the bi-axial cross connector 330, the range of adjustment afforded by the different lengths of the bi-axial cross connector extension rod 342 and the bi-axial cross connector extension plank 346 allows for the bi-axial cross connector 330 to be adjusted from approximately 30 mm to approximately 70 mm spacing between the centerlines of spinal rods 112/114 disposed in the cross connector rod hooks 322. In an embodiment of the bi-axial cross connector 330, spacing between the centerlines of spinal rods 112/114 disposed in the cross connector rod hooks 322 may be adjusted from approximately 34 mm to approximately 37 mm. In a further embodiment of the bi-axial cross connector 330, spacing between the centerlines of spinal rods 112/114 disposed in the cross connector rod hooks 322 may be adjusted from approximately 35 mm to approximately 39 mm. In a further embodiment of the bi-axial cross connector 330, spacing between the centerlines of spinal rods 112/114 disposed in the cross connector rod hooks 322 may be adjusted from approximately 37 mm to approximately 43 mm. In a further embodiment of the bi-axial cross connector 330, spacing between the centerlines of spinal rods 112/114 disposed in the cross connector rod hooks 322 may be adjusted from approximately 41 mm to approximately 51 mm. In a further embodiment of the bi-axial cross connector 330, spacing between the centerlines of spinal rods 112/114 disposed in the cross connector rod hooks 322 may be adjusted from approximately 49 mm to approximately 67 mm. The combination of the multiple specifically disclosed embodiments of the bi-axial cross connector 330 allows for a bi-axial cross connector 330 to be selected suitable for securing spinal rods 112/114 spaced anyplace along the continuum of approximately 34 mm to approximately 67 mm.

Figure 14A:
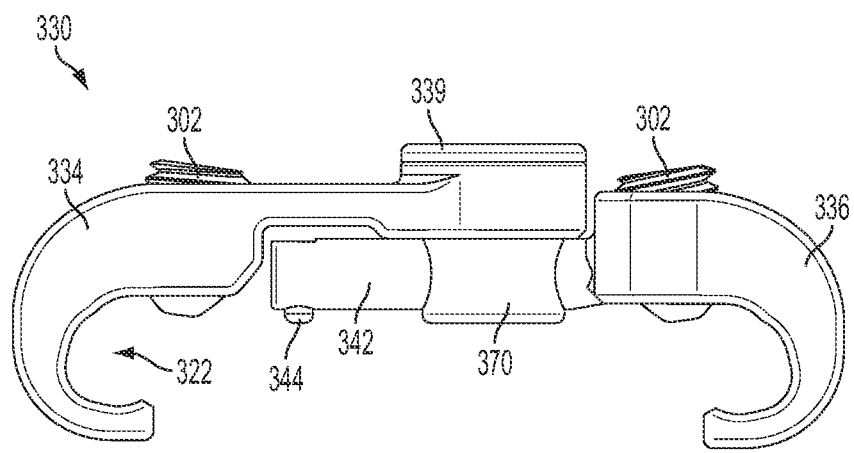
FIG. 14A is a front view of an embodiment of a dual diameter bi-axial cross connector.

Referring to FIG. 14A, an embodiment of a bi-axial cross connector 330. The bi-axial cross connector 330 comprises a first linkage 336, a second linkage 334, a midline locking post 370, a midline locking screw 339, and a pair of conical screws 302. The first linkage 336 and the second linkage 334 can extend along a first axis to lengthen the bi-axial cross connector 330. Adjustment of the length along the first axis allows the bi-axial cross connector 330 to be affixed to spinal rods 112, 114 laterally spaced at any distance along a continuum. This is in contrast to a fixed cross connector 300, wherein the spinal rods must be laterally spaced at approximately one of a finite number of predetermined distances. The first linkage 336 and second linkage 334 may also rotate relative to each other about the first axis. Rotation of the first linkage 336 and second linkage 334 about the first axis allows the bi-axial cross connector 330 to be affixed to spinal rods 112, 114 which are skewed in the sagittal plane. The first linkage 336 and the second linkage 334 are also angulated about a second axis perpendicular to the first axis. Angulation of the first linkage 336 and the second linkage 334 about the second axis allows the bi-axial cross connector 330 to be affixed to spinal rods 112, 114 which are skewed in the coronal plane.

Figure 14B:
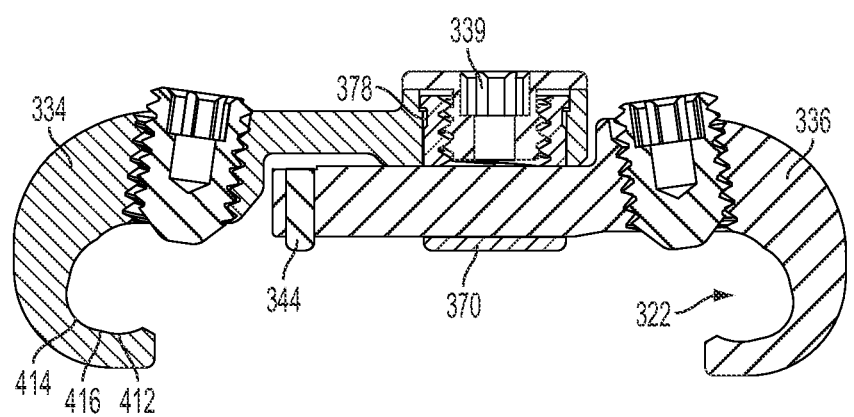
FIG. 14B is a front section view of an embodiment of a dual diameter bi-axial cross connector.

Referring to FIGS. 14A and 14B, the first linkage 336 comprises a cross connector rod hook 322, a bi-axial cross connector extension rod 342, and a bi-axial cross connector extension rod limiter 344. Cross connector rod hook 322 comprises the same geometry as closed rod receiving channel 122 except the upper arc 410 is not present and a portion of middle arc 412 may also be not present. The bi-axial cross connector extension rod 342 is a round shaft with the bi-axial cross connector extension rod limiter 344 disposed on the end. In an embodiment, the bi-axial cross connector extension rod limiter 344 is a pin projecting beyond the diameter of the bi-axial cross connector extension rod 342. The bi-axial cross connector extension rod limiter 344 helps prevent the bi-axial cross connector extension rod 342 from disengaging from the midline locking post 370 during manipulation of the bi-axial cross connector 330. The bi-axial cross connector extension rod limiter 344 is preferably installed in the bi-axial cross connector extension rod 342 subsequent to passing though the midline locking post 370 during the manufacturing and assembly process. The bi-axial cross connector extension rod limiter 344 is preferably sized such that removal of the bi-axial cross connector extension rod 342 from the midline locking post 370 is not feasible.

Figure 14C:
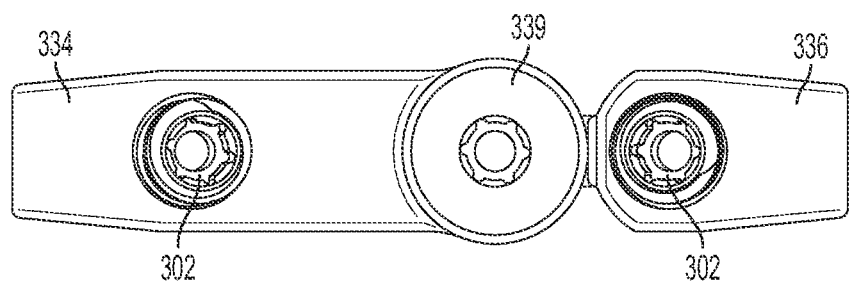
FIG. 14C is a top view of an embodiment of a dual diameter bi-axial cross connector.
Figure 15:
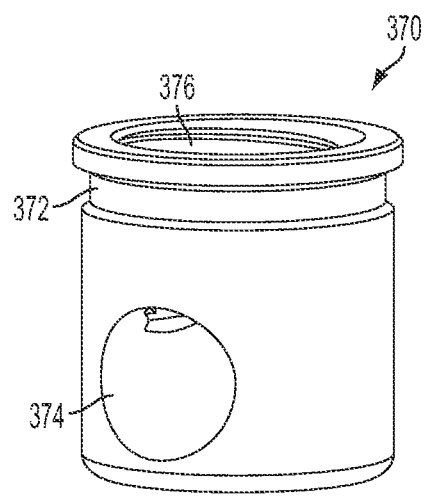
FIG. 15 is an isometric view of an embodiment of a midline locking post post of an embodiment of a dual diameter bi-axial cross connector.

Referring to FIG. 15, an embodiment of the midline locking post 370 used in the embodiment of the bi-axial cross connector 330 shown in FIGS. 14A-14C is shown. The midline locking post 370 comprises a bi-axial cross connector extension rod passage 374, a threaded locking screw receiver 376, and a locking post retention flange 372. The bi-axial cross connector extension rod passage 374 is configured to allow the bi-axial cross connector extension rod 342 to pass through unimpeded but prevent the bi-axial cross connector extension rod limiter 344 from passing through. The threaded locking screw receiver 376 comprises internal threads configured to engage with external threads on the midline locking screw 339. The locking post retention flange 372 retains the midline locking post 370 in the second linkage prior to securing with the midline locking screw.

The second linkage 334 comprises a cross connector rod hook 322, a conical screw receiving port 324 with conical screw receiving threads 326, and a bi-axial cross connector extension plank 346 having a linkage retaining orifice 340. The linkage retaining orifice 340 has a linkage retention flange 378 disposed around the periphery of the linkage retaining orifice 340. The linkage retention flange 378 engages with the locking post retention flange 372.

When assembled, the midline locking screw 339 pulls the midline locking post 370 upward. The movement of the midline locking post 370 moves the first linkage 336 upward as well and compresses the first linkage 336 against the second linkage 334. The compressive force of the midline locking screw 339 and the midline locking post 370 pulling the second linkage 334 and the first linkage 336 together, in conjunction with frictional forces, prevent the bi-axial cross connector 330 from extending along the first axis, rotating about the first axis, or angulating about the second axis.

Referring to FIG. 39, a front profile of a polyaxial screw 230. The polyaxial screw 230 comprises a screw saddle 232 for receiving a spinal rod 112, 114 or lateral connector rod 192 for example. The rod receiving geometry of the screw saddle 232 is envisioned being configured to match the rod receiving geometry of the open rod receiving saddle 222 of the open laminar hook 220 for acceptance of multiple diameter spinal rods including a 5.5 mm diameter spinal rod 112 or a 4.75 mm diameter spinal rod 114. Uniaxial screws with a similar rod receiving geometry for securing multiple diameter spinal rods 112, 114 are also envisioned.

While reference is made throughout this disclosure to dual-diameter connectors, dual-diameter hooks, and dual-diameter screws, it is envisioned that the technique used to allow acceptance of two diameters of rods can be modified to allow three or more diameters of rods.

Figure 16A:
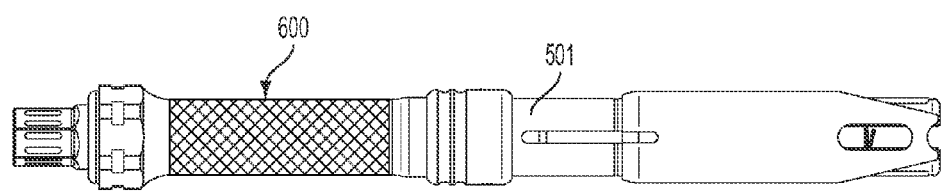
FIG. 16A is a profile view of an embodiment of a rod reduction device.
Figure 16B:
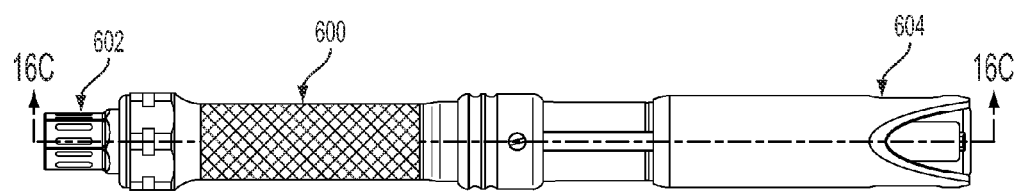
FIG. 16B is a profile view of an embodiment of a rod reduction device.
Figure 16C:
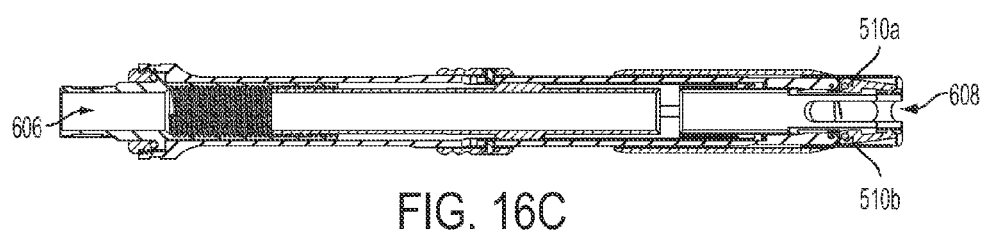
FIG. 16C is a section view of an embodiment of a rod reduction device.

Referring to FIGS. 16A-16C, a rod reduction device 600 is shown. FIG. 16C is a longitudinal cross sectional view of reduction device 600 taken along section line, N-N. In the illustrative embodiment shown, reduction device 600 includes an housing tube 501, advancing knob 502, reduction rod 503, cap 504, inner tube 505, retractor sleeve 506, reduction sleeve 507, release ring 508, release ring screw 509, fingers 510, finger springs 511, spring hinge pins 513, finger cam pins 514, finger hinge pins 515, weld sleeve 516, release spring 517, a plurality of ball bearings 518, and finger cover 519. When assembled together, these components form reduction device 600, which comprises a hollow, cylindrical shaped assembly having a first end 602 and a second end 604. First end 602 includes a first assembly opening 606, and second end 604 includes a second assembly opening 608. Each of the components set forth above will be individually described below herein and shown in separate figures. In addition, it will be shown and described below herein how each of the components of reduction device 600 are interconnected and, once assembled, how reduction device 600 works in operation.

Figure 17A:
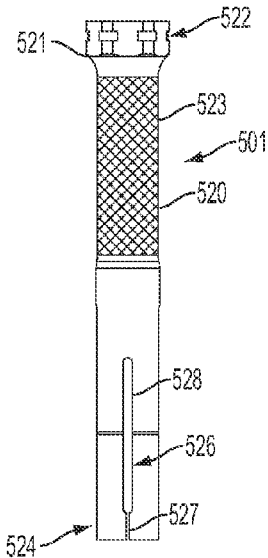
FIG. 17A is a profile view of an embodiment of a housing tube of a rod reduction device.
Figure 17B:
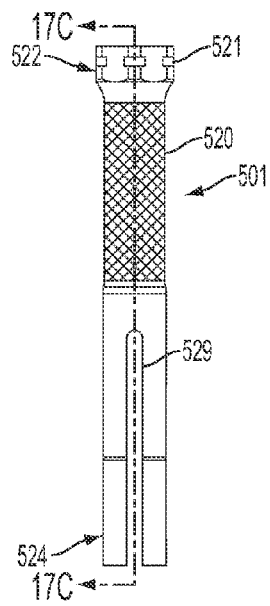
FIG. 17B is a profile view of an embodiment of a housing tube of a rod reduction device.
Figure 17C:
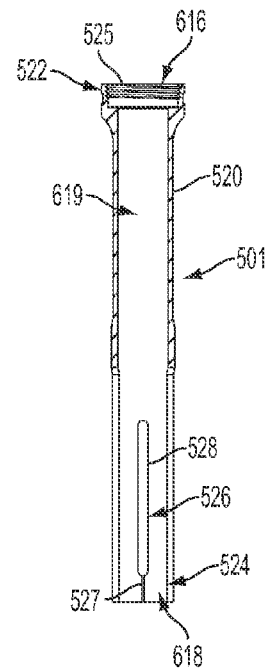
FIG. 17C is a section view of an embodiment of a housing tube of a rod reduction device.

Referring to FIGS. 17A-17C, housing tube 501 of reduction device 600 is shown. Housing tube 501 comprises a hollow, housing tube body 520, having a housing tube first end 522 and a second end 524 opposite housing tube first end 522. Housing tube first end 522 is shaped. In this example, housing tube first end 522 has a hexagonal shape. Additionally, in this example housing tube first end 522 comprises housing tube engagement slots 521. Also, housing tube first end 522 includes internal housing tube threads 525. Housing tube first end 522 also comprises a first housing tube opening 616, and second end 524 comprises a second housing tube opening 618. Housing tube body 520 includes an internal housing tube channel 619 that connects first and second outer tube openings 616/618, respectively.

Housing tube body 520 includes at second end 524 two diametrically opposed housing tube slots 526, each running from the second end 524 longitudinally along at least a portion of housing tube body 520. Housing tube slots 526 further include a narrow portion 527 connected to a wide portion 528.

Housing tube body 520 also includes diametrically opposed second housing tube slots 529 disposed at second end 524, but circumferentially offset 90° from housing tube slots 526. Second housing tube slots 529 run from second end 524 longitudinally along at least a portion of housing tube body 520. Optionally, housing tube body 520 includes a gripping section such as a medium diamond knurl 523 etched into a surface of housing tube body 520.

Figure 18A:
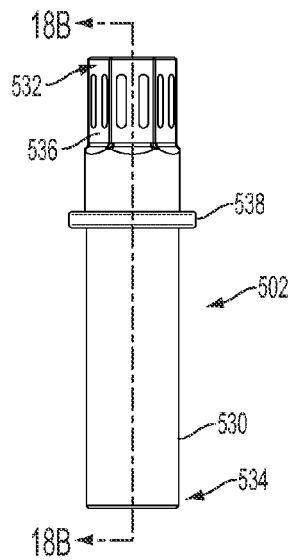
FIG. 18A is a front profile view of an embodiment of an advancing knob of a rod reduction device.
Figure 18B:
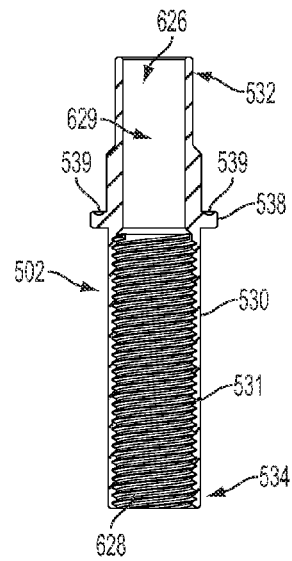
FIG. 18B is a profile view of an embodiment of an advancing knob of a rod reduction device.

Referring to FIGS. 18A and 18B, advancing knob 502 of reduction device 600 is shown. Advancing knob 502 comprises a hollow, advancing knob body 530, having an advancing knob first end 532 and an advancing knob second end 534 opposite advancing knob first end 532. Advancing knob first end 532 is shaped. In this example, advancing knob first end 532 has a hexagonal shape. Advancing knob body 530 also includes an advancing knob annular ring 538 extending therefrom and disposed between a midpoint of advancing knob body 530 and advancing knob first end 532. Advancing knob body 530 includes internal advancing knob threading 531 on a portion of its internal surface. In this example, internal advancing knob threading 531 is disposed from advancing knob second end 534 to just beyond the midpoint of advancing knob body 530 along the internal surface of advancing knob body 530. Advancing knob annular ring 538 further includes an advancing knob bearing well 539 that is disposed within advancing knob annular ring 538 annularly about the circumference of advancing knob body 530. Advancing knob first end 532 also comprises a first advancing knob opening 626, and advancing knob second end 534 comprises a second advancing knob opening 628. Advancing knob body 530 includes an internal advancing knob channel 629 that connects first and second knob openings 626/628, respectively.

Figure 19A:
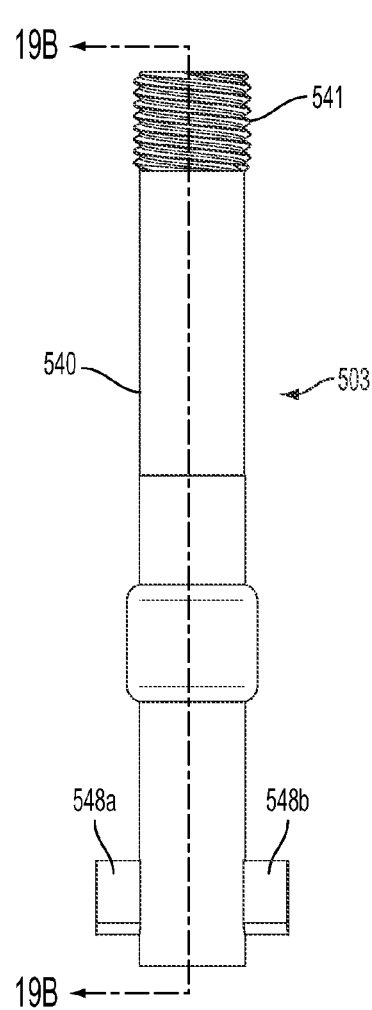
FIG. 19A is a front profile view of an embodiment of a reduction rod of a rod reduction device.
Figure 19B:
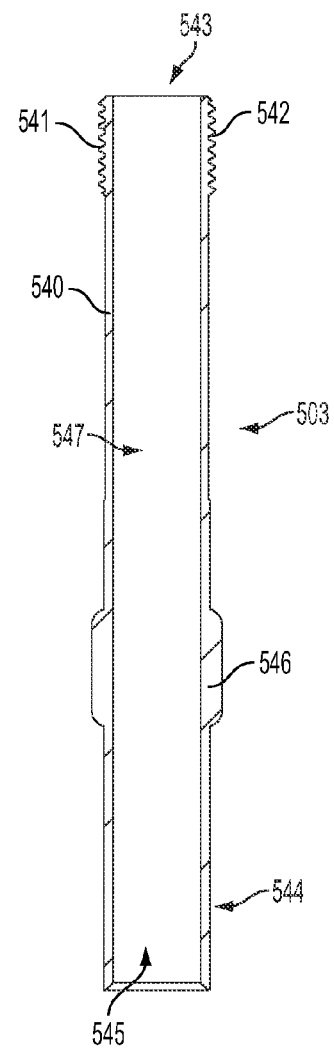
FIG. 19B is a section view of an embodiment of a reduction rod of a rod reduction device.

Referring to FIGS. 19A and 19B, reduction rod 503 of reduction device 600 is shown. Reduction rod 503 comprises a hollow, cylindrical shaped reduction rod body 540, having a first reduction rod end 542 and a second reduction rod end 544 opposite first reduction rod end 542. First reduction rod end 542 comprises a first reduction rod opening 543, and second reduction rod end 544 comprises a second reduction rod opening 545. Reduction rod body 540 includes an internal reduction rod channel 547 that connects first and second reduction rod openings 543/545, respectively. First reduction rod end 542 comprises external reduction rod threads 541 disposed on a portion of the outer surface of reduction rod body 540. A first extender 548a extends radially from the outer surface of reduction rod body 540 adjacent second reduction rod end 544. A second extender 548b extends radially from the outer surface of reduction rod body 540 adjacent second reduction rod end 544 and diametrically opposed to first extender 548a. Reduction rod body 540 also comprises an annular bulbous portion 546 disposed adjacent the midpoint of reduction rod body 540, closer to second reduction rod end 544. Annular bulbous portion 546 has an increased outer diameter compared to the rest of reduction rod body 540.

Figure 20:
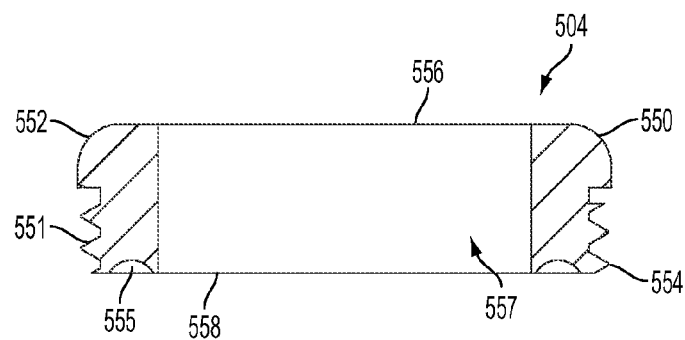
FIG. 20 is a section view of an embodiment of a cap of a rod reduction device.

Referring to FIG. 20, cap 504 of reduction device 600 is shown. Cap 504 comprises a hollow, cylindrical-shaped cap body 550, having a first cap end 552 and a second cap end 554 opposite first cap end 552. First cap end 552 comprises a first cap opening 556, second cap end 554 comprises a second cap opening 558, and cap body 550 includes an internal cap channel 557 that connects first cap opening 556 to second cap opening 558. Also, second cap end 554 includes external cap threads 551 disposed on the outer surface of cap body 550 and a substantially hemispherical channel disposed around the second cap opening 558 to form a cap bearing well 555.

Figure 21A:
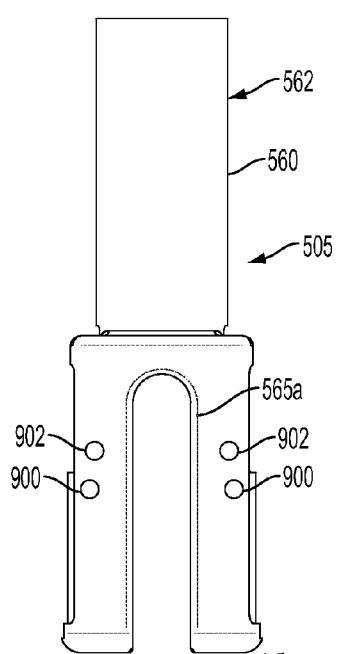
FIG. 21A is a front profile of an embodiment of a inner tube of a rod reduction device.
Figure 21B:
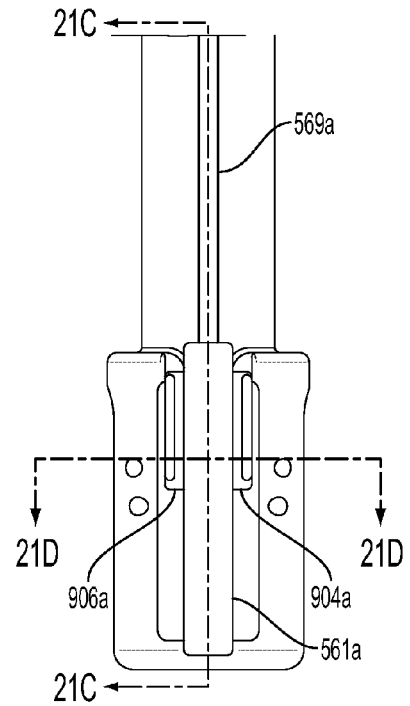
FIG. 21B is a side profile of an embodiment of a inner tube of a rod reduction device.
Figure 21C:
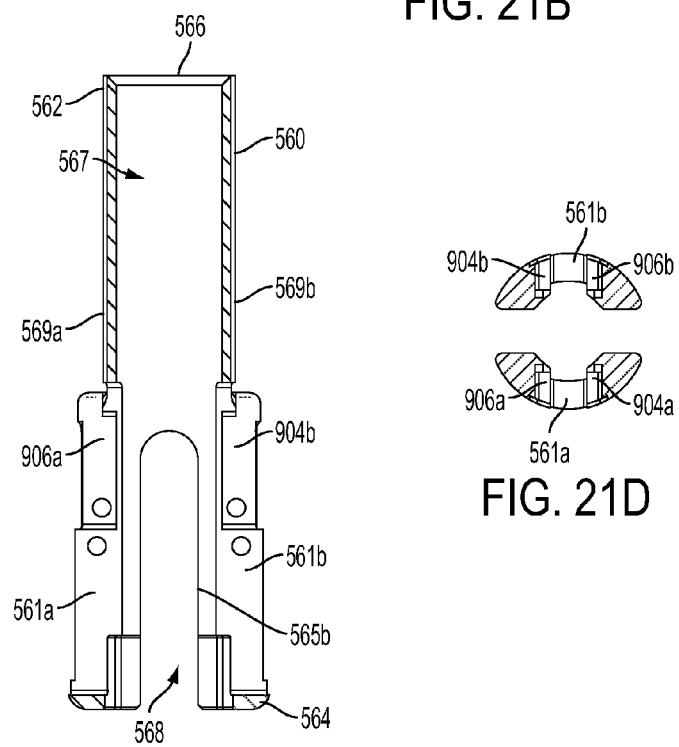
FIG. 21C is a front section view of an embodiment of a inner tube of a rod reduction device.
Figure 21D:
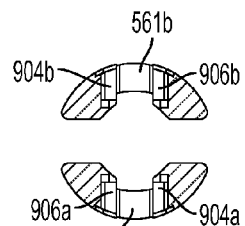
FIG. 21D is a top section view of an embodiment of a inner tube of a rod reduction device.

Referring to FIGS. 21A-21D, inner tube 505 of reduction device 600 is shown. Inner tube 505 comprises a hollow, cylindrical shaped inner tube body 560, having a first inner tube end 562 and a second inner tube end 564 opposite first inner tube end 562. First inner tube end 562 comprises a first inner tube opening 566, and second inner tube end 564 comprises a second inner tube opening 568. Inner tube body 560 includes an internal rod channel 567 that connects first and second inner tube openings 566/568, respectively. As shown in FIGS. 21A and 21C, inner tube 505 comprises a first inner tube slot 565a and a second inner tube slot 565b diametrically opposed to first inner tube slot 565a. Inner tube body 560 also comprises a first inner tube channel 569a and a second inner tube channel 569b as shown in FIG. 21B. Inner tube body 560 comprises a first finger slot 561a and a second finger slot 561b diametrically opposed to first finger slot 561a disposed therein for receiving the fingers 510.

Also, a first left spring pocket 906a and a first right spring pocket 904a are disposed within inner tube body 560, adjacent to and on opposite sides of first finger slot 561a, for receiving finger springs 511. Similarly, a second left spring pocket 906b and a second right spring pocket 904b are disposed within inner tube body 560, adjacent to and on opposite sides of second finger slot 561b, for receiving finger springs 511. In addition, inner tube body 560 comprises finger pin apertures 900 for receiving finger hinge pins 515, and spring pin apertures 902 for receiving spring hinge pins 513.

Referring to FIGS. 22A-22C, retractor sleeve 506 of reduction device 600 is shown. Retractor sleeve 506 comprises a hollow, cylindrical-shaped retractor sleeve body 570, having a first retractor sleeve end 572 and a second retractor sleeve end 574 opposite first retractor sleeve end 572. Retractor sleeve 506 further comprises a first retractor sleeve arm 571 extending longitudinally away from first retractor sleeve end 572 of retractor sleeve body 570 and a second retractor sleeve arm 573 extending longitudinally away from first retractor sleeve end 572, but diametrically opposed to first retractor sleeve arm 571 along the retractor sleeve body 570. Additionally, retractor sleeve 506 comprises a third retractor sleeve arm 575 extending longitudinally away from second retractor sleeve end 574 of retractor sleeve body 570 and a fourth retractor sleeve arm 577 extending longitudinally away from second retractor sleeve end 574, but diametrically opposed to third retractor sleeve arm 575 along retractor sleeve body 570. Additionally, a release spring support ring 578 is formed by a lip disposed around the interior periphery of the retractor sleeve body 570 between the first retractor sleeve end 572 and the second retractor sleeve end 574. The release spring support ring 578 abuts the release spring 517 upon assembly and prevents translation of the release spring.

Referring to FIG. 23, reduction sleeve 507 of reduction device 600 is shown. Reduction sleeve 507 comprises a hollow, cylindrical shaped reduction sleeve body 580, having a first reduction sleeve end 582 and a second reduction sleeve end 584 opposite first reduction sleeve end 582. First reduction sleeve end 582 comprises a first reduction sleeve opening 586, and second reduction sleeve end 584 comprises a second reduction sleeve opening 588. Reduction sleeve body 580 includes an internal reduction sleeve channel 587 that connects first and second reduction sleeve openings 586 and 588, respectively. As shown in the figures, reduction sleeve 507 comprises reduction rod engagement slots 581 running from first reduction sleeve end 582 longitudinally along a portion of reduction sleeve body 580. It is envisioned in an embodiment that there are two reduction rod engagement slots 581 disposed along reduction sleeve body 580 diametrically opposed to each other.

Along the same sides of reduction sleeve body 580 as reduction rod engagement slots 581, reduction sleeve viewing apertures 583 are positioned adjacent to and/or near second reduction sleeve end 584. Reduction sleeve body 580 also comprises a rod engagement radius 585 disposed therein and at the distal end of second reduction sleeve end 584 and another rod engagement radius 585 disposed therein and at the distal end of second reduction sleeve end 584. Reduction sleeve body 580 further comprises reduction sleeve radial reductions 589 disposed therein and at the distal end of second reduction sleeve end 584, offset 90° from rod engagement radii 585.

Referring to FIGS. 24A and 24B, release ring 508 of reduction device 600 is shown. Release ring 508 comprises a hollow, cylindrical shaped release ring body 590, having a first release ring end 592 and a second release ring end 594 opposite first release ring end 592. First release ring end 592 comprises a first release ring opening 596, and second release ring end 594 comprises a second release ring opening 598. Release ring body 590 includes an internal release ring channel 597 that connects first and second release ring openings 596/598, respectively. Additionally, release ring 508 may comprise a first release ring feature 591 disposed within release ring body 590 about the circumference of release ring body 590 and a second release ring feature 593 disposed within release ring body 590 about the circumference of release ring body 590, adjacent to first release ring feature 591. Release ring 508 may also comprise at least one release ring screw aperture 595 disposed within release ring body 590 for receiving release ring screw 509. In an embodiment release ring 508 comprises two diametrically opposed release ring screw apertures 595 for receiving release ring screws 509.

Referring back to FIG. 16C, reduction device 600 comprises a two fingers 510 diametrically opposed to each other. Now referring to FIGS. 25A-25D, finger 510 comprises a finger body 660 having a finger first end 662 and a finger second end 664 opposite finger first end 662. Finger second end 664 comprises a finger hook 661 having a finger hook undercut 663. In one example, finger hook undercut 663 may comprise any angle α above an acute angle. In another example, finger hook undercut 663 may comprise an angle α from about 20° to 90°, from about 30° to about 80°, from about 45° to about 75°. In still another example, finger hook undercut 663 may comprise an angle α from about 40°, about 50°, about 60°, about 70°, about 80°, or about less than 90°.

Finger body 660 comprises a finger aperture 665 disposed therethrough. Finger body 660 also comprises a first finger extension 670 extending longitudinally from finger body 660 and a second finger extension 672 extending longitudinally from finger body 660 opposite to and spaced apart from first finger extension 670. First finger extension 670 comprises a first finger stop 676 disposed at finger first end 662 extending transversely from finger body 660. Second finger extension 672 comprises a second finger stop 678 disposed at finger first end 662 extending transversely from finger body 660.

Figure 25A:
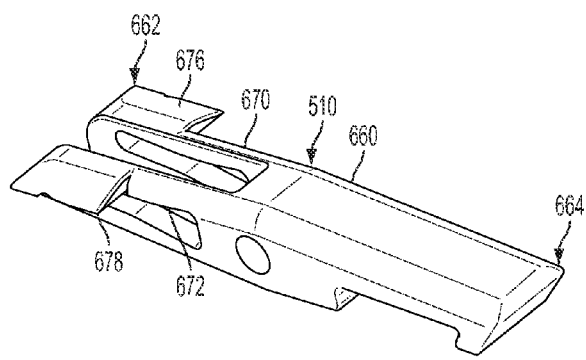
FIG. 25A is an isometric view of an embodiment of a finger of a rod reduction device.
Figure 25B:
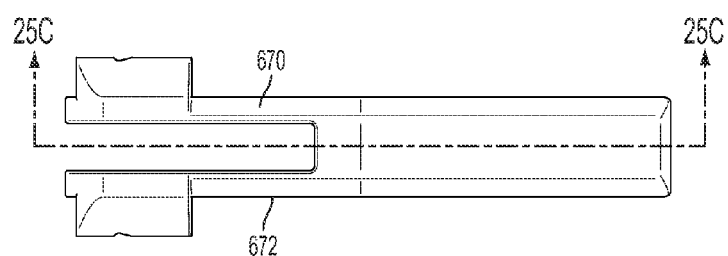
FIG. 25B is a section view of an embodiment of a finger of a rod reduction device.
Figure 25C:
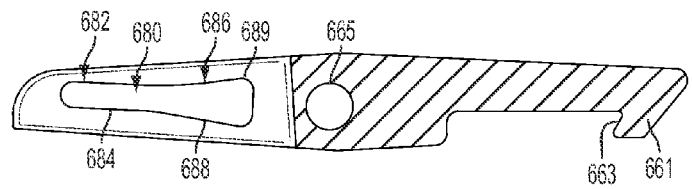
FIG. 25C is a top view of an embodiment of a finger of a rod reduction device.
Figure 25D:
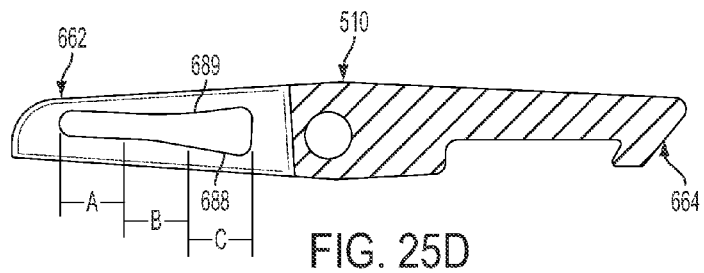
FIG. 25D is a section view of an embodiment of a finger of a rod reduction device.
Figure 26A:
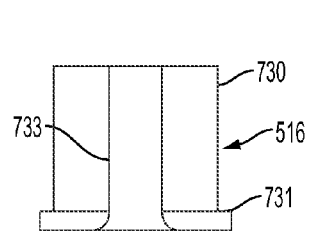
FIG. 26A is a front view of an embodiment of a weld sleeve of a rod reduction device.
Figure 26B:
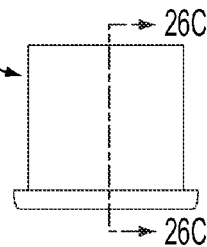
FIG. 26B is a side view of an embodiment of a weld sleeve of a rod reduction device.
Figure 26C:
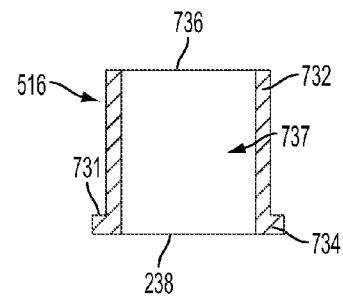
FIG. 26C is a section view of an embodiment of a weld sleeve of a rod reduction device.
Figure 26D:
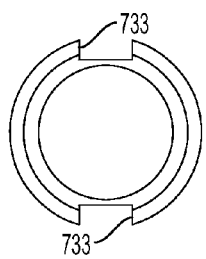
FIG. 26D is a top view of an embodiment of a weld sleeve of a rod reduction device.

Referring specifically to FIG. 25D along with FIGS. 25A-25C, first and second finger extensions 670 and 672 each comprise a finger slot 680. The finger slot 680 comprises three zones: a first zone A, a transition zone B and a third zone C. In particular, first zone A of the slot comprises a width that is configured and sized such that when finger cam pin 514 is positioned within first zone A, finger cam pin 514 forms a running and sliding fit within first zone A. As example, the width of first zone A is defined by upper slot guide 682 and lower slot guide 684 and is sufficient enough to permit finger cam pin 514 to slide within first zone A, but not enough to permit substantial lateral movement transverse to the sliding movement of finger cam pin 514 within first zone A. Substantial lateral movement is defined as movement greater than $1/10^{th}$ the diameter of the finger cam pin 514. Third zone C of finger slot 680 is configured and sized such that it has a width to form a clearance fit with finger cam pin 514. As an example, third zone C is configured to have a funnel shape such that its shape and size creates a smooth transition from the first zone's width to the maximum width of third zone C. Transition zone B provides a smooth transition from the width of the first zone A (i.e., running and sliding fit) to the width of third zone C (i.e., clearance fit). In operation, finger cam pins 514 are positioned within finger slots 680 such that the finger cam pins engage and run along respective inner finger cam surfaces 688 of finger slots 680. This action will be explained in greater detail below herein.

As such, when fingers 510 are in the spring-biased radially inwardly position (i.e., a normal position), finger cam pin 514 are positioned in the third zone C formed by finger cam 686. When reduction device 600 is moved such that second assembly opening 608 is slid over a tulip head of a polyaxial screw 230 or a uniaxial pedicle screw, the tulip head, when inserted into second assembly opening 608, engages the finger hooks 661 of fingers 510 and forces and/or pushes them outwardly against the force of finger springs 511. As the fingers 510 are pushed outwardly, the fingers pivot about finger hinge pins 515 such that finger first ends 662 move radially inward, causing finger cam pins 514 (which are still positioned within third zone C and engaged against respective inner finger cam surfaces 688 to move away from engagement with respective inner finger cam surfaces 688 within third zone C up and, optionally to engagement with respective outer finger cam surface 689. The clearance fit of third zone C provides the clearance to permit the fingers 510 to pivot within rod reduction device 600 in order to permit the tulip head of pedicle screw 230 to insert into second assembly opening 608 of rod reduction device 600.

Referring to FIGS. 26A-26D, weld sleeve 516 is shown. Weld sleeve 516 comprises a hollow, cylindrical-shaped weld sleeve body 730 having a first weld sleeve end 732 and a second weld sleeve end 734. Disposed at first weld sleeve end 732, body comprises a first weld sleeve opening 736, a second weld sleeve opening 738, and an internal weld sleeve channel 737 connecting the two openings. Weld sleeve body 730 comprises diametrically opposed retractor sleeve arm engagement slots 733. Second weld sleeve end 734 includes a weld sleeve flange 731.

Figure 27:
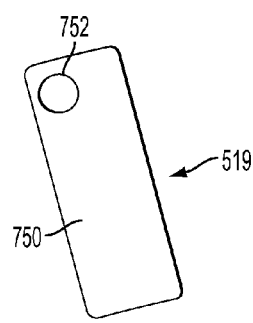
FIG. 27 is an isometric view of an embodiment of a finger cover of a rod reduction device.

Referring to FIG. 27, finger cover 519 of reduction device 600 is shown having a finger cover body 750. Finger cover body 750 includes a finger cover aperture 752 and is curved to closely match the curvature of one or more of the other components.

Figure 28A:
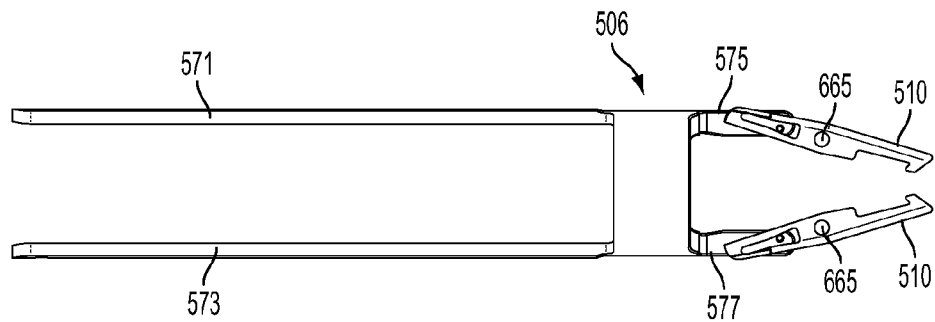
FIG. 28A is a sub-assembly of an embodiment of a rod reduction device.
Figure 28B:
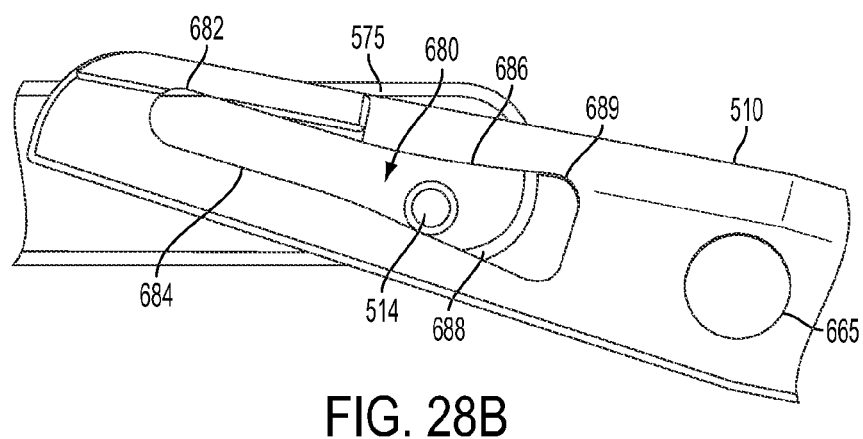
FIG. 28B is a detail view of a sub-assembly of an embodiment of a rod reduction device.

Referring to FIGS. 28A-30C as well as all the figures previously referenced, the assembly of rod reduction device 600 will be described. As shown in FIGS. 28A and 28B, first and second finger extensions 670 and 672 of finger 510 are inserted about third retractor sleeve arm 575 of retractor sleeve 506. Finger cam pin 514 is inserted through finger slot 680 of first finger extension 670, a third retractor sleeve arm cross pin aperture 1000a disposed within third retractor sleeve arm 575, and through finger slot 680 of second finger extension 672. Similarly, first and second finger extensions 670 and 672 of finger 510 are inserted about fourth retractor sleeve arm 577 of retractor sleeve 506. A finger cam pin 514 is also inserted through finger slot 680 of second finger extension 672, a fourth retractor sleeve arm cross pin aperture 1000b disposed within fourth retractor sleeve arm 577, and through finger slot 680 of second finger extension 672.

Figure 29A:
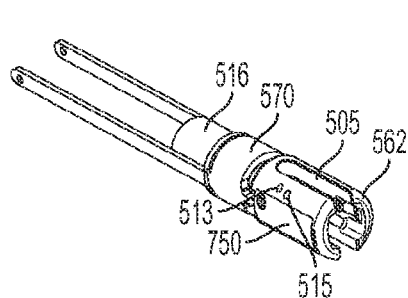
FIG. 29A is a sub-assembly of an embodiment of a rod reduction device.
Figure 29B:
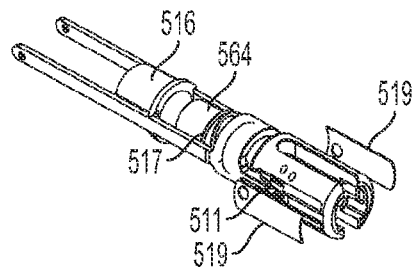
FIG. 29B is a sub-assembly of an embodiment of a rod reduction device.

Referring to FIGS. 29A and 29B, the retractor sleeve 506 and finger 510 assembly is inserted over second inner tube end 564 of inner tube body 560 such that fingers 510 slide into first and second finger slots 561a/561b. Next, as an example, finger springs 511 are placed within first left spring pocket 906a and first right spring pocket 904a. One end of finger spring 511 is abutted against a surface of first right spring pocket 904a and the opposite end of finger spring 511 is abutted against first finger stop 676. One end of finger spring 511 is abutted against a surface of first left spring pocket 906a and the opposite end of finger spring 511 is abutted against second finger stop 678. Finger springs 511 are aligned with spring pin apertures 902 and then spring hinge pins 513 are press fit into the aligned respective spring pin apertures 902 and spring coils. Also, finger aperture 665 is aligned with finger pin aperture 900 and then finger hinge pin 515 is press fit into and through such aligned apertures. The same assembly is performed for the second finger 510. Once assembled, the pins are welded in place using conventional welding processes such as a laser welding process. Pin ends are then polished to be flush with outer surface of inner tube 505.

Figure 32A:
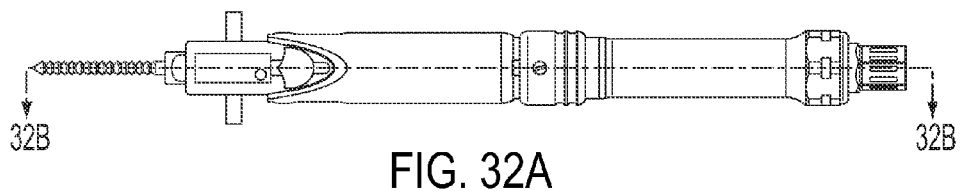
FIG. 32A is a side view of an embodiment of a rod reduction device attached to a spinal pedicle screw.
Figure 32B:
FIG. 32B is a section view of an embodiment of a rod reduction device attached to a spinal pedicle screw.
Figure 32C:
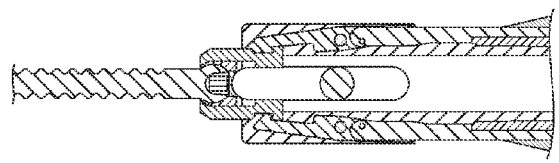
FIG. 32C is a detail section view of an embodiment of a rod reduction device attached to a spinal pedicle screw.

In such a configuration, finger springs 511 bias fingers 510 radially inward toward a central longitudinal axis of reduction device 600 such that finger hook undercuts 663 of fingers 510 engage tulip head pockets 236 disposed within and on opposite sides of the tulip head 234. Tulip head pockets 236 include respective tulip head undercuts 238 that correspond to and engage with finger hook undercuts 163 as shown in FIG. 32B for example.

Release spring 517 is slid over second inner tube end 564 of inner tube body 560 of inner tube 505 as shown in FIG. 29B. Next, align retractor sleeve arm engagement slots 733 of weld sleeve 516 with respective first and second arms 571/573 of retractor sleeve 506 and then slide weld sleeve 516 over second inner tube end 564 of inner tube body 560 until weld sleeve flange 731 of weld sleeve 516 is flush with retractor sleeve body 570 as shown in FIGS. 29A and 29B. Finger cover bodies 750 are fit into respective first and second finger slots 561a/561b as shown in FIGS. 29A and 29B and then may be connected to inner tube body 560 in any number of conventional means such as, for example, welding (e.g., laser welding around periphery of finger cover), snap-fit, etc.

Referring to FIGS. 16A-16C and 530, release ring 508 is slid over housing tube 501. Reduction rod 503 is inserted into housing tube 501 as shown in FIG. 30 such that first and second extenders 548a/548b of reduction rod 503 are inserted through and extend from housing tube slots 526 of housing tube 501. Next, retractor sleeve 506/inner tube 505/weld sleeve 516/fingers 510 assembly shown in FIGS. 29A and 29B is inserted into second end 524 of housing tube 501 such that first and second arms 571/573 of retractor sleeve 506 align with and slide into second housing tube slots 529 of housing tube 501 as shown in FIG. 30. Weld sleeve 516 is connected to housing tube 501 via conventional connection methods, including welding. Additionally, first and second screws 509a/509b are inserted through and threadably engaged with release ring 508, housing tube 501, and respective first and second retractor sleeve arms 571/573. Engagement with first retractor sleeve arm 571 and second retractor sleeve arm 573 is through first retractor sleeve arm screw aperture 579a and second retractor sleeve arm screw aperture 579b respectively.

Figure 30A:
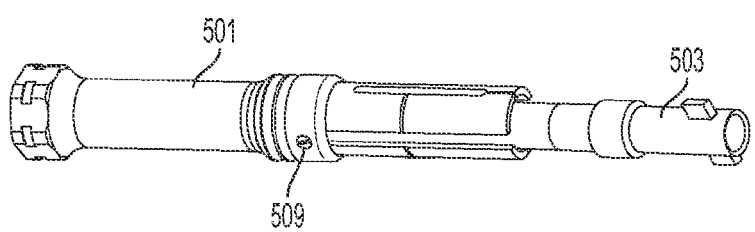
FIG. 30A is a sub-assembly of an embodiment of a rod reduction device.
Figure 30B:
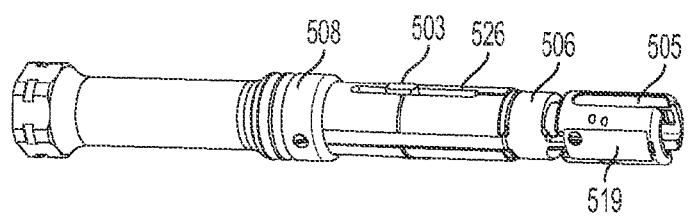
FIG. 30B is a sub-assembly of an embodiment of a rod reduction device.
Figure 30C:
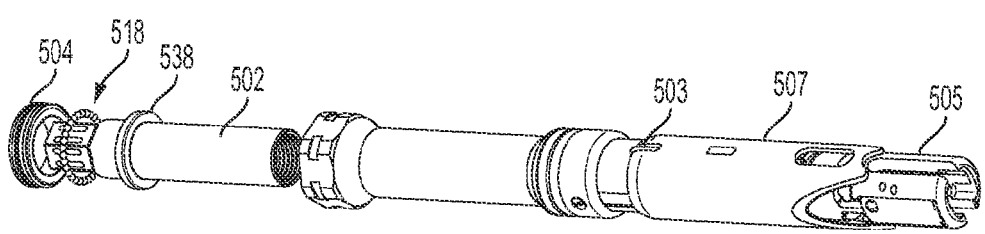
FIG. 30C is an exploded view of an embodiment of a rod reduction device.

Referring to FIGS. 30A-30C, the final assembly of reduction device 600 is shown. Specifically, reduction sleeve 507 is slid over second end 524 of housing tube 501 such that reduction rod engagement slots 581 abut against and are welded to first and second extenders 548a and 548b of reduction rod 503. Advancing knob 502 is inserted into housing tube first end 522 of housing tube 501, a plurality of ball bearings 518 are disposed into advancing knob bearing well 539 of advancing knob annular ring 538 of advancing knob 502, and then cap 504 is threadably engaged to housing tube first end 522 of housing tube 501. The cap bearing well 555 interfaces with the ball bearings 518 opposite the advancing knob bearing well 539.

Figure 33A:
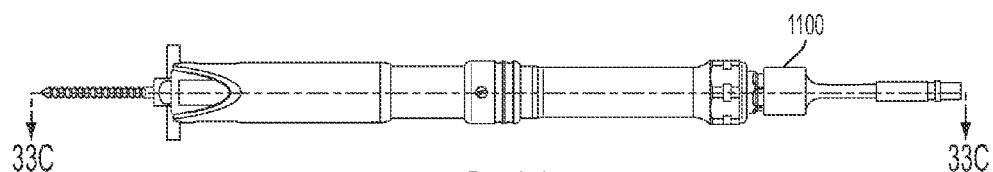
FIG. 33A is a side view of an embodiment of a rod reduction device attached to a spinal pedicle screw with the reduction sleeve engaging a spinal rod.
Figure 33B:
FIG. 33B is a section view of an embodiment of a rod reduction device attached to a spinal pedicle screw with the reduction sleeve engaging a spinal rod.
Figure 33C:
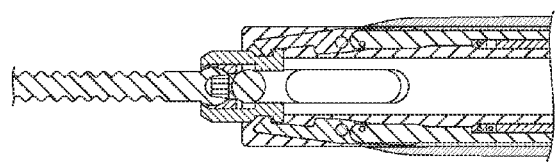
FIG. 33C is a detail section view of an embodiment of a rod reduction device attached to a spinal pedicle screw with the reduction sleeve engaging a spinal rod.

Referring to FIGS. 33A and 33B, a reduction adaptor 1100 is shown. Reduction adaptor 1100 includes at a first end, an internal hexagonal head (e.g., similar to a socket head), and at a second end, an external hexagonal end, opposite the first end. It is understood that other types, configurations, and shapes of heads can be used. The first end can be inserted onto advancing knob first end 532 of advancing knob 502 to engage advancing knob engagement head 536 of advancing knob 502 as shown in FIGS. 33A and 33B.

Referring to FIGS. 40A-40C, an embodiment of pedicle screw 230, size and shape of the pedicle screw 230 and the second assembly opening 608 of the reduction device 600 substantially match. When the tulip head 234 of the pedicle screw 230 is inserted into second assembly opening 608 of second end 604 of device 600 the pedicle screw 230 is engaged with minimal freedom of movement. As such, in one embodiment, the clocking of reduction device 600 to the tulip head 234 of the pedicle screw 230 is from about 0° to about 20°, from about 0° to about 15°, from 0° to about 10°, or from 0° to about 5°. As shown, fingers 510 are engaging respective tulip head pockets 236 of the tulip head 234. The tulip head 234 and corresponding second assembly opening 608 of device 600 has a cross sectional shape that is substantially rectilinear, having rounded corners and curved sidewalls.

Figure 31:
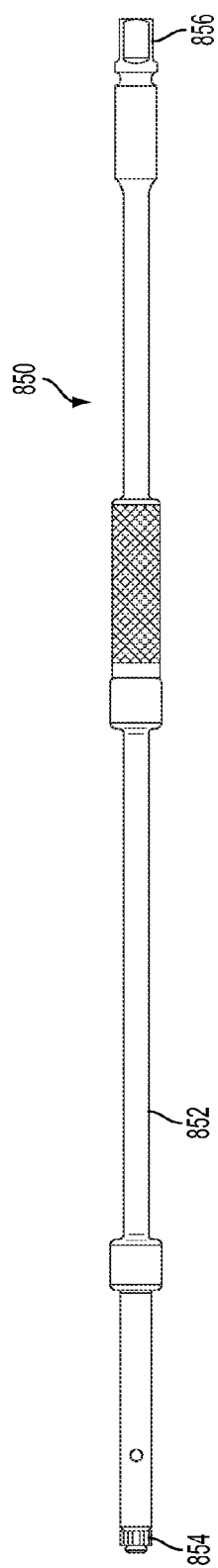
FIG. 31 is a front profile view of an embodiment of a set screw driver.

Referring to FIG. 31, a set screw driver 850 is shown. Set screw driver 850 includes a set screw driver body 852 having a set screw engagement head 854 and a driver head 856. In this example, set screw engagement head 854 includes an external head that has a star-shape which matches and/or corresponds with the internal star-shaped head of the set screw. Driver head 856 comprises a substantially square-shaped head. However, it is understood that the heads of the driver and/or the set screw head can have either internal and/or external heads having any shape, size, and/or configuration.

A method for reducing a rod within a tulip head of a pedicle screw using the reduction device 600 is shown and described herein. FIGS. 32A-34C are sequential steps in the process of this method for reducing a spinal rod 112/114 into a tulip head 234 of a pedicle screw 230. Such a method may be part of a method for correcting or ameliorating spinal aberrations or defects such as, for example, scoliosis, lordosis, and/or kyphosis.

FIGS. 32A-34C show the tulip head of pedicle screw 230 fully inserted into second assembly opening 608 of reduction device 600 and in locked engagement, i.e., fingers 510 are fully inserted into respective tulip head pockets 236 on opposite sides of the tulip head 234 such that finger hook undercuts 663 of the fingers 510 are engaged with respective tulip head undercuts 238 of the tulip head pockets 236 of the tulip head 234. In the embodiment shown in FIGS. 40A-40C, the tulip head pockets 236 of the tulip head 234 do not extend transversely all the way across the tulip head. Thus, in this illustrative example, the tulip head pockets 236 have an upper wall which includes the tulip head undercut 238, a lower wall, and two opposed side walls. However, it is understood that other configurations may be utilized such as, for example, no side walls and/or bottom wall.

When release ring 508 is pulled toward first end 602 of device 600, it pulls retractor sleeve 506 respective toward first end 602 which causes finger cam pins 514 to slide along inner finger cam surfaces 688 from third zone C through transition zone B and into first zone A, pulling fingers 510 radially outwardly from the tulip head. When the finger cam pins 514 have slide into zone C, fingers 510 are moved into the unlock position, disengaging finger hook undercuts 663 from the corresponding tulip head undercuts 238 of the tulip head pockets 236 of the tulip head 234. In this unlocked position, the tulip head 234 may be removed from the reduction device 600.

Referring to FIGS. 35A and 35B, an embodiment of a rod reduction assembly 450 is shown. Advancing wheel 456 is in threaded engagement with outer reducer shell 454. Rotation of advancing wheel 456 forces movement of reduction arm 452 relative to the outer reducer shell 454.

Figure 36A:
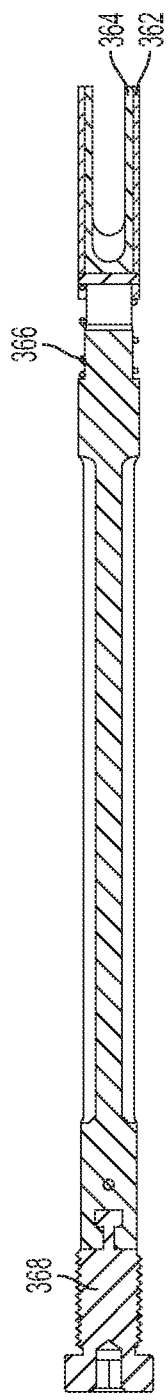
FIG. 36A is a section view of an embodiment of a provisional locking instrument.
Figure 36B:
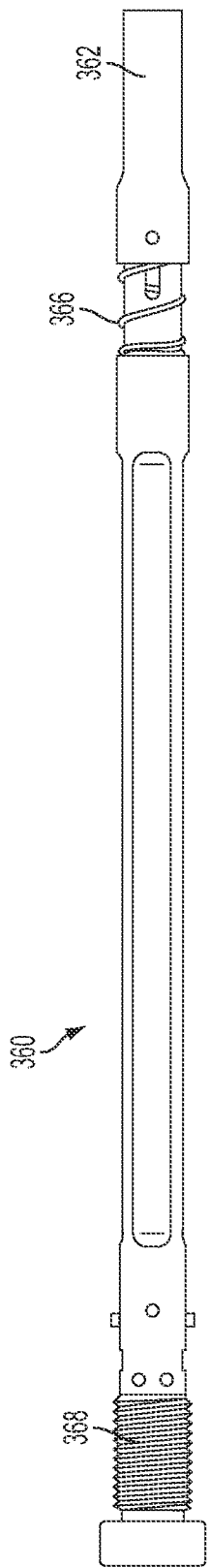
FIG. 36B is a profile view of an embodiment of a provisional locking instrument.

Referring to FIGS. 36A and 36B, an embodiment of a provisional locking instrument 360 is shown. The provisional locking instrument 360 is inserted into the central shaft of the rod reduction assembly 450 and provisional locking instrument threads 368 are engaged with internal rod reduction threads 458. The threaded engagement advances the provisional locking assembly through the rod reduction assembly 450. The provisional locking instrument 360 further comprises a locking sheath 362 which engages the tulip head 234 of a pedicle screw 230 advances the tulip head undercuts 238 against flanged catches of the reduction arm 452. As the provisional locking instrument 360 is advanced, the locking sheath 362 engages the tulip head 234 and ceases advancing. Continued advancing of the provisional locking instrument 360 exposes polyaxial locking tines 364 which engage the screw shaft locking mechanism of the pedicle screw 230. The polyaxial locking tines 364 are generally concealed by the locking sheath 362 which is held in a forward position by an advancing spring 366.

Referring to FIGS. 37A-38, an embodiment of a pedicle screw inserter 380 is shown. The pedicle screw inserter 380 is used to insert a pedicle screw, for example a polyaxial screw 230, into a patient. The pedicle screw inserter 380 comprises a central tightening shaft 382, a handle 384, a friction sleeve 386, and a screw head engagement sleeve 388. The central tightening shaft 382 has a driver tip 394 shaped to match the drive head of the pedicle screw shaft. For example. The driver tip 394 may be a hexalobe. The screw head engagement sleeve 388 has screw head engagement threads 390. The screw head engagement threads mate with the internal threads of a pedicle screw to secure the screw head engagement sleeve 388 and a pedicle screw together. The handle 384 and friction sleeve 386 allow for free rotation of the central tightening shaft 382.

To insert a pedicle screw the screw head engagement sleeve 388 is engaged with the head of a pedicle screw. The driver tip 394 of the central tightening shaft 382 is aligned with the mating feature of the pedicle screw. The friction sleeve 386 and handle 384 are moved along the central tightening shaft until the friction sleeve interlocks with the head of the pedicle screw as shown in FIG. 38. The central tightening shaft 382 is rotated which rotates the shaft of the pedicle screw through the engagement with the driver tip 394. The interlock between the friction sleeve 386 and the head of the pedicle screw helps prevent the screw head engagement sleeve from unthreading during the pedicle screw insertion process. The friction sleeve 386 and central tightening shaft 382 rotate in unison as they are both engaged with the head of the pedicle screw.

An exemplary method of therapy for use of the present devices is described as follows:

Initially, the area of implantation is surgically approached.

For a pedicle screw correction technique, a thoracic facetectomy is performed. The facet joints are cleaned and rongeurs are used to perform a partial inferior articular process osteotomy. This is done to enhance visualization. 3 mm to 5 mm of the inferior facet is removed and the articular cartilage of the superior facets is removed, except for on the lowest vertebra to be instrumented. This allows for the intraoperative localization of the thoracic pedicle screw starting points and enhances fusion.

The pedicles are subsequently prepared. A pedicle awl or burr is used to create a 3 mm deep posterior cortical breach. The pedicle awl may be advanced by gently twisting the handle with light pressure. A pedicle blush may be visualized suggesting entrance into the cancellous bone at the base of the pedicle but the blush may not be evident when preparing small pedicles due to the limited intrapedicular cancellous bone. When no pedicle blush is visualized, use a straight or curved pedicle probe, a Lenke probe for example, to search in the cortical breach for the soft, funnel-shaped cancellous bone, which indicates the entrance to the pedicle. This procedure should be performed with the tip of the pedicle probe pointed laterally to avoid perforation of the medial cortex. Gripping the sides of the handle to avoid applying too much ventral pressure, the tip of the probe is inserted approximately 2 mm to approximately 25 mm. The probe is oriented so that the flat surface of the probe is in the same plane as the curve of the pedicle, then removed and reinserted with the tip pointed medially. The probe is advanced to the desired depth and rotated approximately 180° to ensure adequate room for a screw. The feeler probe is advanced to the base of the hole, alternatively called the floor, to confirm five distinct bony borders. The five bony borders being a floor and four walls (medial, lateral, superior, and inferior). When necessary, bone wax or other hemostatic agent may be placed in the pedicle hole to limit bleeding, and then the probe may be repositioned with a more appropriate trajectory.

The pedicle is undertapped for the appropriate screw size. After the pedicle is undertapped a flexible feeler probe may be used to verify presence of threads in the tapped hole. To measure the length of the hole, a feeler probe is advanced to the floor of the hole and a hemostat is clamped to the feeler probe at the point where it exits the pedicle. The appropriate screw diameter and length may subsequently be selected based on both preoperative measurement and intraoperative observation. The same technique is repeated for each of the remaining pedicles that need to be instrumented.

Roentgenographic assistance using plain radiographs or fluoroscopy may be utilized to ensure proper screw trajectory. Pedicle markers are placed into the holes of the pedicles and a lateral view is obtained. An anterior-posterior view may also be obtained.

Pedicle screws 230 are placed in each prepared pedicle. Selection of uniaxial or polyaxial screws 230 is at the discretion of the surgeon with both options being anticipated. The screws should be advanced slowly through the pedicle to ensure proper tracking. The pedicle screws 230 should be placed at every segment that allows free passage of a pedicle screw on the correction side of the spine and every third or fourth level on the supportive side. At the proximal and distal end of the supportive side at least two screws should be inserted. Addition of more screws will result in greater construct rigidity. Upon placement of the screws they should be checked radiographically to ensure intraosseous screw placement. Should it be determined that a pedicle is too narrow to cannulate, alternate fixation methods such as hooks 210, 220, wires or tapes may be used.

Once correct pedicle screw placement has been verified radiographically, the spinal rods 112, 114 are prepared. The spinal rods 112, 114 are measured and contoured in the sagittal and coronal planes. When contouring, the spinal rods 112, 114 may be clamped at both ends with rod grippers to help prevent the rod from rotating.

Once prepared to the proper contour and length, the first rod is placed into the previously inserted screws. To reduce the rod and seat it into each previously placed pedicle screw a rocker, a rod reduction assembly 450, or a reduction device 600 may be used. The rocker method is an effective method for reducing the rod into the implant when only a slight height difference exists between the rod and the implant saddle. To reduce the rod using the rocker method, the sides of the implant are grasped with the rocker cam above the rod. The rocker is levered backwards over the rod to seat the rod into the saddle of the implant. A set screw is subsequently placed and provisionally tightened to hold the rod in place.

For reduction of the rod using the rod reduction assembly 450, with the pedicle screw and rod in place the rod reduction assembly is applied over the head of the screw. The provisional locking instrument 360 is inserted down the tube of the rod reduction assembly 450 and threaded down to engage the provisional locking feature. Alternatively, the provisional locking instrument 360 may be inserted down the tube of the rod reduction assembly 450 and partially threaded down prior to affixing the rod reduction assembly to the screw head. The rod is then reduced by turning the advancing wheel 456 of the rod reduction assembly 450. If greater torque is required to reduce the rod, a reduction adaptor 1100 attached to an axial or torque limiting T-handle may interface with the advancing wheel 456 of the rod reduction assembly 450. The provisional locking instrument is subsequently removed as the rod reduction assembly has taken over the provisional lock engagement. A set screw driver 850 is used to introduce a set screw. The set screw is passed down the central cavity of the rod reduction assembly 450 until it bottoms out on the screw threads. To avoid cross threading of the set screw, the set screw is turned counterclockwise until a click is felt and then turned clockwise to tighten.

For reduction of the rod using the rod reduction device 600, with the pedicle screw and rod on place the red reduction device is applied over the tulip head 234 of the screw. The fingers 510 of the rod reduction device 600 engage the tulip head pockets 236 of the pedicle screw tulip head 234. The rod is then reduced by turning the advancing knob 502 of the rod reduction device 600. If greater torque is required to reduce the rod, a reduction adaptor 1100 attached to an axial or torque limiting T-handle may interface with the advancing knob 502 of the rod reduction device 600. A set screw driver 850 is used to introduce a set screw. The set screw is passed through the first assembly opening 606 of the rod reduction device 600 until it bottoms out on the screw threads. To avoid cross threading of the set screw, the set screw is turned counterclockwise until a click is felt and then turned clockwise to tighten.

While leaving the set screws loose or only locked at one end, the spinal rod 112, 114 is slowly straightened using tubular benders. Fully straightening the spinal rod 112, 114 may require several passes.

Once the contoured rod and all the set screws have been placed, the contoured rod is rotated into its final position. The rotation must be done slowly to prevent rapid neurologic changes and/or injury to the spinal cord. Using two rod holders the contoured rod is rotated into the desired position. The apical set screws are tightened and compression or distraction may be performed. During all the correction maneuvers the screw and bone interface should be monitored.

The second rod and its respective set screws are placed according to the techniques previously outlined. Following placement of the second rod and set screws, convex compressive forces are placed on the segments using a parallel compressor to horizontalize the lowest instrumented vertebra and mildly compress the convexity of the deformity. It is preferred that compression be released just prior to final tightening. This technique helps ensure that the implant head and rod are normalized to one another and allows for the rod to be fully seated in the implant head during the final tightening step.

With all rods and screw placed and provisionally secured with set screws, the set screws are tightened to their final torque. The counter torque wrench and the set screw driver 850 are placed onto the open screw, saddle, and set screw. A torque limiting T-handle is placed on the set screw driver 850 and turned clockwise while firmly holding the counter torque wrench. The torque liming T-handle is preferably set to 70 in-lbs. The T-handle is turned clockwise until an audible click is heard indicating the proper torque has been met.

After final tightening of the set screws, cross connectors are placed. The cross connector connection provides rotational stability to the construct as a framed construct resists rotational forces. The cross connectors should be placed close to the construct extremities but placement at other positions along the construct is also envisioned.

Bi-axial cross connectors 330 are affixed to the spinal rods 112, 114 by capturing a rod in each of the cross connector rod hooks 322 at the end of each linkage 334, 336. Prior to attaching the bi-axial cross connector 330 to the spinal rods 112, 114 the midline nut 338 or midline locking screw 339 is provisionally tightened. A first rod is captured in the cross connector rod hook 322 at the end of one of the linkages 334, 336 and the conical screw 302 is provisionally tightened to anchor the device to the rod. The midline nut 338 or midline locking screw 339 is loosened to allow the linkages 334, 336 to angulated and lengthen or shorten. A second rod is captured in the cross connector rod hook 322 at the end of the other linkage 334, 336 and the conical screw 302 is provisionally tightened. The midline nut 338 or midline locking screw 339 is re-tightened to secure the linkages 334, 336 of the bi-axial cross connector 330. For final tightening of the conical screw 302, the counter torque tube and screw driver are placed onto the bi-axial cross connector 330, spinal rod 112, 114, and conical screw. A torque limiting T-handle is placed on the driver shaft and turned clockwise while firmly holding the counter torque wrench. The torque liming T-handle is preferably set to 50 in-lbs. The T-handle is turned clockwise until an audible click is heard indicating the proper torque has been met.

Fixed cross connectors 300 are affixed to the spinal rods 112, 114 by placing the fixed cross connector over the rods such that a rod is seated in each cross connector rod hook 322. The conical screws 302 are provisionally tightened and then finally tightened using a counter torque tube, driver shaft, and torque limiting T-handle as with the bi-axial cross connectors 330. For some applications, the fixed cross connector extension rod 304 of the fixed cross connector 300 may need to be bent to fit the anatomy and spinal rod 112, 114 arrangement.

For a hook 210, 220 based correction technique, the surgical site is prepared by dividing the facet capsule. A portion of the inferior facet process may also be removed to facilitate insertion of the hook 210, 220. The pedicle should be clearly identified with the help of a pedicle elevator. The pedicle hook may be inserted from T1 to T10 with the hook blade 212 cephalad and in the infralaminar position. The hook blade 212 of the hook 210, 220 should wrap around the pedicle and not split the inferior articular process. To assist in position the pedicle hook, a hook pusher may be utilized.

For hook placement at the transverse process a wide blade hook is typically used in a pedicle-transverse claw construct as a caudal hook. Laminar hook trials may be used to separate the ligamentous attachment between the undersurface of the transverse process and the posterior arch of the rib medial to the rib-transverse joint. The hook is then inserted using a hook holder.

For placement of thoracic hooks a partial or total division of the spinous process directly above the vertebra to be instrumented may be performed. A division and/or partial removal of the ligamentum flavum and a small laminotomy are carried out on the superior lamina. The amount of bone removed from the lamina may vary depending on the size of the hook blade 212 and throat angle chosen. The upper edge of the lamina below or the lower edge of the lamina above may be resected to ease placement of the hook 210, 220. A laminar hook trial may also be used to check the space between laminar and peridural structures. When placing a hook 210, 220 on the superior lamina a hook should be used to insert the hook.

With all the appropriate hooks placed on the side of the deformity to be corrected, a rod template is used to measure the length and curve. The spinal rod 112, 114 on the corrective side should be cut 2-3 cm longer than the actual length to leave adequate length for correction. The spinal rod 112, 114 is then bent into the correct orientation using a french bender or tubular benders.

Any hooks 210, 220 which are not stable prior to spinal rod 112, 114 insertion should be removed until placement of the rod.

The spinal rod 112, 114 and set screws 120 are placed and provisionally tightened according to the same technique outlined for pedicle screws. Rotation, in-situ bending, compression, and distraction maneuvers may be completed undertaken. During rod rotation it is important to monitor the interval hooks as they tend to back out.

Upon completion of the deformity correction and the seating of the correction rod, the opposite side of the construct is prepared. Using a french bender, the rod for the opposite side of the construct is contoured according to the curvature of the spine and the residual position of alignment from the correction rod. The contoured rod is placed into the hooks 210, 220 with the rod holder or by hand and provisionally secured with set screws 120. With the spinal rod 112, 114 secured to the implants, distraction and/or compression is performed to place the hooks 210, 220 into their final position. The set screws 120 are subsequently finally tightened according to the technique previously discussed for pedicle screws and cross connectors 300, 330.

Cross connectors 300, 330 are preferably also added to the construct for added rotational stability.

This is simply an exemplary surgical technique and other known and accepted methods or techniques for performing steps outlined within the technique may be substituted where appropriate.

The previous text sets forth a broad description of numerous different embodiments. The description is to be construed as exemplary only and does not describe every possible embodiment since describing every possible embodiment would be impractical, if not impossible, and it will be understood that any feature, characteristic, component, step or methodology described herein can be deleted, combined with or substituted for, in whole or part, any other feature, characteristic, component, step or methodology described herein. Numerous alternative embodiments could be implemented, using either current technology or technology developed after the filing date of this patent, which would still fall within the scope of the claims.

It should also be understood that, unless a term is expressly defined in this specification using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). No term is intended to be essential unless so stated. To the extent that any term recited in the claims at the end of this patent is referred to in this patent in a manner consistent with a single meaning, that is done for sake of clarity only so as to not confuse the reader, and it is not intended that such a claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph or similar doctrine.

It is also noted that recitations herein of "at least one" component, element, etc., should not be used to create an inference that the alternative use of the articles "a" or "an" should be limited to a single component, element, etc.

It is noted that recitations herein of a component of the present disclosure being "configured" to embody a particular property, or function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

It is noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Rather, the claims appended hereto should be taken as the sole representation of the breadth of the present disclosure and the corresponding scope of the various inventions described herein. Further, it will be apparent that modifications and variations are possible without departing from the scope of the invention defined in the appended claims. More specifically, although some aspects of the present disclosure are identified herein as preferred or particularly advantageous, it is contemplated that the present disclosure is not necessarily limited to these aspects.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made. It is therefore intended to cover in the appended claims all such changes and modifications.

The invention claimed is:

1. A medical instrument, the medical instrument comprising a rod reduction assembly and a pedicle screw engaging assembly; wherein,
   the rod reduction assembly comprises a rod reduction sleeve, a reduction rod, and an advancing knob;
   the reduction sleeve comprises a hollow, cylindrical shaped body having an internal reduction sleeve channel, reduction rod engagement slots on a first end, and rod engagement radii on a second end;
   the reduction rod comprises external reduction rod threads on a first end and first and second extenders extending radially from an outer surface proximal a second end;
   the first and second extenders engage with the reduction rod engagement slots;
   the advancing knob comprises internal threads matched to the external reduction rod threads;
   the pedicle screw engaging assembly comprises fingers for engagement with the head of a pedicle screw, finger cam pins, an inner tube, and a release ring;
   the fingers each comprise a finger hook having a finger hook undercut, a finger slot, and a finger aperture;
   the finger slot having a first end distal the finger hook with a width sufficient to permit finger cam pin to slide through without substantial lateral movement transverse to the sliding direction and a second end proximal the finger hook with a larger width to form a clearance fit with the finger cam pin;
   the finger aperture disposed between the finger hook and the finger slot;
   the inner tube comprises a hollow, cylindrical body having a first inner tube end and a second inner tube end, a first inner tube slot and a second inner tube slot diametrically opposed across the cylindrical body, and a first finger slot and a second finger slot diametrically opposed across the cylindrical body;
   the first inner tube slot and the second inner tube slot are open toward the second inner tube end;
   the fingers are disposed in the first finger slot and the second finger slot with the fingers oriented to dispose the finger hooks proximal the second inner tube end and the finger hook undercuts toward an interior of the inner tube; and
   movement of the release ring from a first position to a second position moves the finger cam pins from the second end of the finger slot to the first end of the finger slot thereby positioning the fingers for insertion of the head of a pedicle screw.

2. The medical instrument of claim 1, wherein the pedicle screw engaging assembly further comprises finger springs to bias the finger hooks toward the interior of the inner tube.

3. The medical instrument of claim 1, wherein the first finger slot and second finger slot are circumferentially offset 90 degrees from the first inner tube slot and the second inner tube slot.

4. The medical instrument of claim 1, wherein the finger hook undercut comprises an angle between approximately 20 degrees and 90 degrees.

5. The medical instrument of claim 1, wherein the pedicle screw engaging assembly further comprises a retractor sleeve mechanically connecting the release ring and the fingers; the retractor sleeve comprising a first retractor sleeve arm and a second retractor sleeve arm with first and second retractor sleeve arm screw apertures for connection of the release ring and a third retractor sleeve arm and a fourth retractor sleeve arm with third and fourth retractor sleeve arm cross pin apertures for connection to the fingers via the finger cam pins.

6. The medical instrument of claim 1, wherein the reduction rod further comprises an annular bulbous portion with an increased outer diameter compared to the rest of the reduction rod.

7. The medical instrument of claim 1, wherein the medical instrument further comprises finger covers disposed over the first finger slot and the second finger slot to conceal and protect the fingers.

8. A rod reduction device comprising:
a rod reduction sleeve, a reduction rod, an advancing knob, an inner tube, fingers; finger cam pins, and a release ring, wherein:
the reduction sleeve comprises a hollow, cylindrical shaped body having an internal reduction sleeve channel, reduction rod engagement slots on a first end, and rod engagement radii on a second end;
the reduction rod comprises external reduction rod threads on a first end and first and second extenders extending radially from an outer surface proximal a second end;
the first and second extenders engage with the reduction rod engagement slots;
the advancing knob comprises internal advancing knob threading matched to the external reduction rod threads;
the inner tube comprises a hollow, cylindrical body having a first inner tube end, a second inner tube end, a first inner tube slot, a second inner tube slot diametrically opposed across the cylindrical body, a first finger slot, and a second finger slot diametrically opposed to the first finger slot;
the fingers are each disposed within respective first and second finger slots for engagement with a head of a pedicle screw;
the fingers each comprise a finger hook having a finger hook undercut, a finger slot, a finger first end, a finger second end, and a finger aperture;
the finger slot having a first end adjacent to the finger first end with a width sufficient to permit one of the finger cam pins to slide through without substantially lateral movement transverse to the sliding direction and a second end proximal the finger hook with a larger width to form a clearance fit with the finger cam pin;
the finger aperture disposed between the finger hook and the finger slot;
the first inner tube slot and the second inner tube slot are open toward the second inner tube end;
the fingers are disposed in the first finger slot and the second finger slot with the fingers oriented to dispose the finger hooks proximal the second inner tube end and the finger hook undercuts toward an interior of the inner tube; and
movement of the release ring from a first position to a second position moves the finger cam pins from a second end of the finger slot to the first end of the finger slot thereby positioning the fingers for insertion of the head of a pedicle screw.

9. The rod reduction device of claim 8, further comprises finger springs to bias the finger hooks toward the interior of the inner tube.

10. The rod reduction device of claim 8, wherein the first finger slot and second finger slot are circumferentially offset 90 degrees from the first inner tube slot and the second inner tube slot.

11. The rod reduction device of claim 8, wherein the finger hook undercut comprises an angle between approximately 20 degrees and 90 degrees.

12. The rod reduction device of claim 8, further comprises a retractor sleeve mechanically connecting the release ring and the fingers; the retractor sleeve comprising a first retractor sleeve arm and a second retractor sleeve arm with first and second retractor sleeve arm screw apertures for connection of the release ring, and a third retractor sleeve arm and a fourth retractor sleeve arm with third and fourth retractor sleeve arm cross pin apertures for connection to the fingers via the finger cam pins.

13. The rod reduction device of claim 8, wherein the reduction rod further comprises an annular bulbous portion with an increased outer diameter compared to the rest of the reduction rod.

14. The rod reduction device of claim 8, further comprises finger covers disposed over the first finger slot and the second finger slot to conceal and protect the fingers.

* * * * *